US009345486B2

(12) United States Patent
Zhang et al.

(10) Patent No.: US 9,345,486 B2
(45) Date of Patent: May 24, 2016

(54) NANOFIBROUS CONDUITS FOR NERVE REGENERATION

(75) Inventors: Miqin Zhang, Bothell, WA (US); Narayan Bhattarai, Seattle, WA (US)

(73) Assignee: University of Washington, Seattle, WA (US)

( * ) Notice: Subject to any disclaimer, the term of this patent is extended or adjusted under 35 U.S.C. 154(b) by 475 days.

(21) Appl. No.: 12/404,879

(22) Filed: Mar. 16, 2009

(65) Prior Publication Data
US 2010/0234863 A1 Sep. 16, 2010

(51) Int. Cl.
*A61B 17/11* (2006.01)
*A61L 27/26* (2006.01)
*D01D 5/00* (2006.01)
A61B 17/04 (2006.01)
A61B 17/00 (2006.01)

(52) U.S. Cl.
CPC ............ *A61B 17/1128* (2013.01); *A61L 27/26* (2013.01); *D01D 5/0007* (2013.01); *A61B 17/04* (2013.01); *A61B 2017/00526* (2013.01); *A61L 2430/32* (2013.01); *D10B 2211/20* (2013.01)

(58) Field of Classification Search
CPC ..... A61L 2430/32; A61L 27/26; A61L 27/20; A61L 27/58; A61L 27/56; A61B 17/1128; A61B 17/04; A61B 2017/00526; C08L 5/08; D01D 5/0015; D01D 5/003; D01D 5/0038; D01D 5/0046
USPC .......... 606/151–153, 228–231; 424/422–437; 623/23.72–23.76; 536/20
See application file for complete search history.

(56) References Cited

U.S. PATENT DOCUMENTS

| 4,822,361 | A | * | 4/1989 | Okita et al. ................. 623/23.71 |
| 4,870,966 | A | * | 10/1989 | Dellon et al. .................. 606/152 |
| 4,963,146 | A | * | 10/1990 | Li .................... 606/152 |
| 5,019,087 | A | | 5/1991 | Nichols |
| 5,026,381 | A | | 6/1991 | Li |
| 5,120,802 | A | * | 6/1992 | Mares et al. ................... 525/415 |
| 5,147,399 | A | * | 9/1992 | Dellon et al. ................. 606/152 |
| 5,217,495 | A | * | 6/1993 | Kaplan et al. .............. 623/13.18 |
| 5,306,550 | A | * | 4/1994 | Nishiyama et al. ........... 442/340 |
| 5,897,821 | A | * | 4/1999 | Kawasaki ..................... 264/186 |
| 6,517,933 | B1 | * | 2/2003 | Soane et al. .................. 428/221 |

(Continued)

FOREIGN PATENT DOCUMENTS

| JP | 04-82918 A | 3/1992 |
| WO | 2004035885 A1 | 4/2004 |

(Continued)

OTHER PUBLICATIONS

Malheiro et al., New poly(e-caprolectone)/chitosan blend fibers for tissue engineering applications, Jul. 14, 2009, Acta Biomaterialia.*

(Continued)

*Primary Examiner* — Dianne Dornbusch
(74) *Attorney, Agent, or Firm* — Christensen O'Connor Johnson Kindness PLLC

(57) ABSTRACT

A hollow fibrous conduit for promoting regeneration of a severed nerve, comprising a first end for coapting the conduit to a first end of a severed nerve and second end for coapting the conduit to a second end of the severed nerve, the hollow fibrous conduit comprising chitosan-poly(caprolactone) fibers. Methods for making the conduit and methods for using the conduit for nerve regeneration.

19 Claims, 14 Drawing Sheets

(56) References Cited

U.S. PATENT DOCUMENTS

| | | | |
|---|---|---|---|
| 6,676,675 B2 | 1/2004 | Mallapragada | |
| 6,753,454 B1 | 6/2004 | Smith | |
| 7,108,721 B2 * | 9/2006 | Huckle et al. | 623/23.74 |
| 7,910,690 B2 * | 3/2011 | Ringeisen et al. | 528/502 D |
| 7,964,210 B2 * | 6/2011 | Wang et al. | 424/426 |
| 7,967,855 B2 * | 6/2011 | Furst et al. | 623/1.42 |
| 8,147,858 B2 | 4/2012 | Zhang | |
| 8,460,692 B2 | 6/2013 | Zhang | |
| 2002/0136848 A1 * | 9/2002 | Yoshii et al. | 428/35.7 |
| 2003/0017208 A1 | 1/2003 | Ignatious | |
| 2003/0060836 A1 * | 3/2003 | Wang et al. | 606/152 |
| 2003/0157047 A1 * | 8/2003 | Lennon et al. | 424/70.11 |
| 2003/0176876 A1 * | 9/2003 | Chen et al. | 606/152 |
| 2003/0203003 A1 * | 10/2003 | Nelson et al. | 424/426 |
| 2004/0018226 A1 | 1/2004 | Wnek | |
| 2004/0058887 A1 | 3/2004 | Bowlin | |
| 2004/0197311 A1 * | 10/2004 | Brekke et al. | 424/93.7 |
| 2005/0013844 A1 | 1/2005 | Hadlock | |
| 2005/0106211 A1 * | 5/2005 | Nelson et al. | 424/423 |
| 2005/0136253 A1 | 6/2005 | Michael | |
| 2005/0267565 A1 * | 12/2005 | Dave et al. | 623/1.15 |
| 2006/0083784 A1 | 4/2006 | Ignatious | |
| 2006/0195179 A1 * | 8/2006 | Sun et al. | 623/1.54 |
| 2007/0010831 A1 * | 1/2007 | Romero-Ortega et al. | 606/152 |
| 2007/0100358 A2 * | 5/2007 | Romero-Ortega et al. | 606/152 |
| 2007/0134305 A1 * | 6/2007 | Zilberman | 424/443 |
| 2007/0202148 A1 * | 8/2007 | Ringeisen et al. | 424/423 |
| 2008/0089922 A1 | 4/2008 | Cheng | |
| 2008/0125870 A1 | 5/2008 | Carmichael | |
| 2009/0076530 A1 * | 3/2009 | Fukutomi et al. | 606/151 |
| 2009/0087469 A1 * | 4/2009 | Zhang et al. | 424/422 |
| 2010/0303881 A1 * | 12/2010 | Hoke et al. | 424/423 |
| 2011/0035023 A1 * | 2/2011 | Maquet et al. | 623/23.65 |

FOREIGN PATENT DOCUMENTS

| | | | | |
|---|---|---|---|---|
| WO | 2004113513 A3 | 12/2004 | | |
| WO | 2005000169 A2 | 1/2005 | | |
| WO | 2007080590 A2 | 7/2007 | | |
| WO | WO 2007/112446 | * 10/2007 | | A61L 15/28 |
| WO | 2009142770 A2 | 1/2010 | | |
| WO | 2010059778 A1 | 5/2010 | | |
| WO | 2010090513 A2 | 8/2010 | | |

OTHER PUBLICATIONS

Shalumon et al., Single step electrospinning of chitosan/poly(caprolactone) nanofibers using formic acid/acetone solvent mixture, Dec. 3, 20009, Carbohydrate Polymers.*

Garcia Cruz et al., Blending polysaccharides with biodegradable polymers. I. Properties of chitosan/polycaprolactone blends, Oct. 15, 2007, Journal of Biomaterials Research Part B: Applied Biomaterials.*

Chen et al, Mechanical and viscoelastic properties of chitin fiber reinforced poly(e-caprolactone),Dec. 16, 2004, European Polymer Journal 41 (2005) 453-457.*

She et al, Preparation and characterization of polycaprolactone-chitosan composites for tissue engineering applications, Jun. 12, 2007, Journal Material Science (2007) 42:8113-8119.*

Chen et al., Electrospun chitosan-P(LLA-CL) nanofibers for biomimetic extracellular matrix, 2008, Journal of Biomaterials Science, Polymer Edition, 19:5, 677-691.*

Yang et al., Mechanical properties and interfacial interaction of a novel bioabsorbable chitin fiber reinforced poly(e-caprolactone) composite, 2001, Journal of Material Science Letters 20, 977-979.*

Prabhakaran et al., Electrospun biocomposite nanofibrous scaffold for neural tissue enginering, 2008, Tissue Engineering Part A, vol. 14, No. 11.*

Sarasam et al. "Characterization of chitosan-polycaprolactone blends for tissue engineering applications", Apr. 7, 2005, Biomaterials, vol. 26, p. 5500-5508.*

Sarasam et al. "Blending Chitosan with Polycaprolactone: Effects on Physicochemical and Antibacterial Properties", 2006, Biomacromolecules, vol. 7, p. 1131-1138.*

Ren et al. The enzymatic degradation and swelling properties of chitosan matrices with different degrees of N-acetylation, Aug. 18, 2005, Carbohydrate Research, vol. 340, p. 2403-2410.*

Belkas, J.S., et al., "Peripheral Nerve Regeneration Through Guidance Tubes," Neurological Research 26(2):151-160, Mar. 2004.

Bellamkonda, R.V., "Peripheral Nerve Regeneration: An Opinion on Channels, Scaffolds and Anisotropy," Biomaterials 27(19):3515-3518, Jul. 2006.

Bhattarai, N., et al., "Electrospun Chitosan-Based Nanofibers and Their Cellular Compatibility," Biomaterials 26(31):6176-6184, Nov. 2005.

Bini, T.B., et al., "Electrospun Poly(L-Lactide-Co-Glycolide) Biodegradable Polymer Nanofibre Tubes for Peripheral Nerve Regeneration," Nanotechnology 15(11):1459-1464, Nov. 2004.

Chew, S.Y., et al., "Aligned Protein—Polymer Composite Fibers Enhance Nerve Regeneration: A Potential Tissue-Engineering Platform," Advanced Functional Materials 17(8):1288-1296, May 2007.

Honma, T., et al., "Poly(E-Caprolactone)/Chitin and Poly(ε-Caprolactone)/Chitosan Blend Films With Compositional Gradients: Fabrication and Their Biodegradability," Macromolecular Bioscience 6(3):241-249, Mar. 2006.

Prabhakaran, M.P., et al., "Surface Modified Electrospun Nanofibrous Scaffolds for Nerve Tissue Engineering," Nanotechnology 19(45):1-8, Nov. 2008.

Mo, X.M., et al., "Electrospun (P(LLA-CL) Nanofiber: A Biomimetic Extracellular Matrix for Smooth Muscle Cell and Endothelial Cell Proliferation," Biomaterials 25(10):1883-1890, May 2004.

Mohammadi, Y., et al., "Nanofibrous Poly(ε-caprolactone)/poly(vinyl alcohol)/Chitosan Hybrid Scaffolds for Bone Tissue Engineering Using Mesenchymal Stem Cells," International Journal of Artificial Organs 30(3):204-211, Mar. 2007.

Monzingo, A.F., "Chitinases, Chitosanases, and Lysozymes Can Be Divided Into Procaryotic and Eucaryotic Families Sharing a Conserved Core," Nature Structural Biology 3(2):133-140, Feb. 1996.

Murayama, Y., et al., "Cellular Responses of Bioabsorbable Polymeric Material and Guglielmi Detachable Coil in Experimental Aneurysms," Stroke 33(4):1120-1128, Apr. 2002.

Nehrer, S., et al., "Chondrocyte-Seeded Collagen Matrices Implanted in a Chondral Defect in a Canine Model," Biomaterials 19(24):2313-2328, Dec. 1998.

Nishio, Y., and R. St. John Manley, "Blends of Cellulose With Nylon 6 and Poly(ε-Caprolactone) Prepared by a Solution-Coagulation Method," Polymer Engineering and Science 30(2):71-82, Jan. 1990.

Pattison, M.A., et al., "Three-Dimensional, Nano-Structured PLGA Scaffolds for Bladder Tissue Replacement Applications," Biomaterials 26(15):2491-2500, May 2005.

Pham, Q.P., et al., "Electrospinning of Polymeric Nanofibers for Tissue Engineering Applications: A Review," Tissue Engineering 12(5):1197-1211, May 2006.

Rho, K.S., et al., "Electrospinning of Collagen Nanofibers: Effects on the Behavior of Normal Human Keratinocytes and Early-Stage Wound Healing," Biomaterials 27(8):1452-1461, Mar. 2006.

Rowley, J.A., et al., "Alginate Hydrogels as Synthetic Extracellular Matrix Materials," Biomaterials 20(1):45-53, Jan. 1999.

Rydevik, B., et al., "Biomechanics of Peripheral Nerves and Spinal Nerve Roots," in M. Nordin et al. (eds.), "Basic Biomechanics of the Musculoskeletal System," Lippincott, Philadelphia, 2004, Chap. 5, pp. 127-146.

Schmidt, C.E., and J.B. Leach, "Neural Tissue Engineering: Strategies for Repair and Regeneration," Annual Review of Biomedical Engineering 5:293-347, 2003.

Shields, K.J., et al., "Mechanical Properties and Cellular Proliferation of Electrospun Collagen Type II," Tissue Engineering 10(9/10):1510-1517, Sep.-Oct. 2004.

Suh, J.-K. F., and H.W.T. Matthew, "Application of Chitosan-Based Polysaccharide Biomaterials in Cartilage Tissue Engineering: A Review," Biomaterials 21(24):2589-2598, Dec. 2000.

Taravel, M.N., and A. Domard, "Relation Between the Physicochemical Characteristics of Collagen and Its Interactions With Chitosan: I," Biomaterials 14(12):930-938, Oct. 1993.

(56) References Cited

OTHER PUBLICATIONS

Temenoff, J.S., and A.G. Mikos, "Review: Tissue Engineering for Regeneration of Articular Cartilage," Biomaterials 21(5):431-440, Mar. 2000.
Tripathy, T., et al., "Novel Flocculating Agent Based on Sodium Alginate and Acrylamide," European Polymer Journal 35(11):2057-2072, Nov. 1999.
Tuzlakoglu, K., et al., "Nano- and Micro-Fiber Combined Scaffolds: A New Architecture for Bone Tissue Engineering," Journal of Materials Science: Materials in Medicine 16(12):1099-1104, Dec. 2005.
Woodfield, T.B.F., et al., "Scaffolds for Tissue Engineering of Cartilage," Critical Reviews™ in Eukaryotic Gene Expression 12(3):209-236, 2002.
Yamane, S., et al., "Feasibility of Chitosan-Based Hyaluronic Acid Hybrid Biomaterial for a Novel Scaffold in Cartilage Tissue Engineering," Biomaterials 26(6):611-619, Feb. 2005.
Yang, J., et al. "Hepatocyte-Specific Porous Polymer-Scaffolds of Alginate/Galactosylated Chitosan Sponge for Liver-Tissue Engineering," Biotechnology Letters 23(17):1385-1389, Sep. 2001.
Yang, S., et al., "The Design of Scaffolds for Use in Tissue Engineering. Part I. Traditional Factors," Tissue Engineering 7(6):679-689, Dec. 2001.
Young, A.P., and A.J. Wagers, "Pax3 Induces Differentiation of Juvenile Skeletal Muscle Stem Cells Without Transcriptional Upregulation of Canonical Myogenic Regulatory Factors," Journal of Cell Sciences 123(15):2632-2639, Aug. 2010.
Zhang, R., and P.X. MA, "Synthetic Nano-Fibrillar Extracellular Matrices With Predesigned Macroporous Architectures," Journal of Biomedical Materials Research 52(2):430-438, Nov. 2000.
Zhang, S., "Beyond the Petri Dish," Nature Biotechnology 22(2):151-152, Feb. 2004.
Zhang, S., "Fabrication of Novel Biomaterials Through Molecular Self-Assembly," Nature Biotechnology 21(10):1171-1178, Oct. 2003.
Zhang, Y., et al., "Recent Development of Polymer Nanofibers for Biomedical and Biotechnological Application," Journal of Materials Science: Materials in Medicine 16(10):933-946, Oct. 2005.
Alsberg, E., et al., "Cell-Interactive Alginate Hydrogels for Bone Tissue Engineering," Journal of Dental Research 80(11):2025-2029, Nov. 2001.
Amiji, M., and K. Park, "Surface Modification of Polymeric Biomaterials With Poly(ethylene oxide), Albumin, and Heparin for Reduced Thrombogenicity," Journal of Biomaterial Science, Polymer Edition 4(3):217-234, 1993.
Beier, J.P., et al., "Collagen Matrices From Sponge to Nano: New Perspectives for Tissue Engineering of Skeletal Muscle," BMC Biotechnology 9:34, Apr. 2009, 14 pages.
Bhattarai, N., et al., "Alginate-Based Nanofibrous Scaffolds: Structural, Mechanical, and Biological Properties," Advanced Materials 18(11):1463-1467, Jun. 2006.
Bhattarai, N., et al., "Natural-Synthetic Polyblend Nanofibers for Biomedical Applications," Advanced Materials 21(27):2792-2797, Jul. 2009.
Bognitzki, M., et al., "Preparation of Fibers With Nanoscaled Morphologies: Electrospinning of Polymer Blends," Polymer Engineering and Science 41(6):982-989, Jun. 2001.
çaykara, T., et al., "Poly(ethylene oxide) and Its Blends With Sodium Alginate," Polymer 46(24):10750-10757, Nov. 2005.
Chalfoun, C.T., et al., "Tissue Engineered Nerve Constructs: Where Do We Stand?" Journal of Cellular and Molecular Medicine 10(2):309-317, Apr. 2006.
Chamberlain, L.J., et al., "Collagen-Gag Substrate Enhances the Quality of Nerve Regeneration Through Collagen Tubes up to Level of Autograft," Experimental Neurology 154(2):315-329, Dec. 1998.
Chew, S.Y., et al., "The Role of Electrospinning in the Emerging Field of Nanomedicine," Current Pharmaceutical Design 12(36):4751-4770, 2006. (Author manuscript PMCID: PMC2396225, available in PMC May 25, 2008, 33 pages).
Ciardelli, G. and V. Chiono, "Materials for Peripheral Nerve Regeneration," Macromolecular Bioscience 6(1):13-26, Jan. 2006.

Cooper, A., et al., "Polymeric Fibrous Matrices for Substrate-Mediated Human Embryonic Stem Cell Lineage Differentiation," Macromolecular Bioscience 12(7):882-892, Jul. 2012.
Dar, A., et al., "Optimization of Cardiac Cell Seeding and Distribution in 3D Porous Alginate Scaffolds," Biotechnology and Bioengineering 80(3):305-312, Nov. 2002.
Deitzel, J.M., et al., "Controlled Deposition of Electrospun Poly(ethylene oxide) Fibers," Polymer 42(19):8163-8170, Sep. 2001.
Doolabh, V.B., et al., "The Role of Conduits in Nerve Repair: A Review," Reviews in the Neurosciences 7(1):47-84, Jan.-Mar. 1996.
Dzenis, Y., "Material Science. Spinning Continuous Fibers for Nanotechnology," Science 304(5679):1917-1919, Jun. 2004.
El-Hadi, A., et al., "Correlation Between Degree of Crystallinity, Morphology, Glass Temperature, Mechanical Properties and Biodegradation of Poly (3-hydroxyalkanoate) PHAs and Their Blends," Polymer Testing 21(6):665-674, 2002.
Ellis-Behnke, R.G., et al., "Nano Neuro Knitting: Peptide Nanofiber Scaffold for Brain Repair and Axon Regeneration With Functional Return of Vision," Proceedings of the National Academy of Sciences of the USA (PNAS) 103(13):5054-5059, Mar. 2006.
Elsdale, T., and J. Bard, "Collagen Substrata for Studies on Cell Behavior," Journal of Cell Biology 54(3):626-687, Sep. 1972.
Frenot, A., and I.S. Chronakis, "Polymer Nanofibers Assembled by Electrospinning," Current Opinion in Colloid and Interface Science 8(1):64-75, Mar. 2003.
Gross, R.A., and B. Kalra, "Biodegradable Polymers for the Environment," Science 297(5582):803-807, Aug. 2002.
Gugala, Z., and S. Gogolewski, "In Vitro Growth and Activity of Primary Chondrocytes on a Resorbable Polyactide Three-Dimensional Scaffold," Journal of Biomedical Materials Research 49(2):183-191, Feb. 2000.
Hartgerink, J.D., et al., "Peptide-Amphiphile Nanofibers: A Versatile Scaffold for the Preparation of Self-Assembling Materials," Proceedings of the National Academy of Sciences of the USA (PNAS) 99(8):5133-5138, Apr. 2002.
Hashimoto, T., et al., "Development of Alginate Wound Dressings Linked With Hybrid Peptides Derived From Laminin and Elastin," Biomaterials 25(7-8):1407-1414, Mar. 2004.
Hollister, S.J., "Porous Scaffold Design for Tissue Engineering," Nature Materials 4(7):518-524, Jul. 2005.
Hsu, S.-H., et al., "Evaluation of Chitosan-Alginate-Hyaluronate Complexes Modified by an Rgd-Containing Protein as Tissue-Engineering Scaffolds for Cartilage Regeneration," Artificial Organs 28(8):693-703, Aug. 2004.
Huang, Z.-M., et al., "A Review on Polymer Nanofibers by Electrospinning and Their Applications in Nanocomposites," Composites Science and Technology 63(15):2223-2253, Nov. 2003.
Hutmacher, D.W., et al., "An Introduction to Biodegradable Materials for Tissue Engineering Applications," Annals, Academy of Medicine, Singapore 30(2):183-191, Mar. 2001.
Iozzo, R.V., and A.D. Murdoch, "Proteoglycans of the Extracellular Environment: Clues From the Gene and Protein Side Offer Novel Perspectives in Molecular Diversity and Function," FASEB Journal 10(5):598-614, Apr. 1996.
Iwasaki, N., et al., "Feasibility of Polysaccharide Hybrid Materials for Scaffolds in Cartilage Tissue Engineering: Evaluation of Chondrocyte Adhesion to Polyion Complex Fibers Prepared From Alginate and Chitosan," Biomacromolecules 5(3):828-833, May 2004.
Jiang, M., et al., "Interpolymer Complexation and Miscibility Enhancement by Hydrogen Bonding," Advances in Polymer Science 146:121-196, May 1999.
Johnson, E.O., et al., "Regeneration and Repair of Peripheral Nerves," Injury, International Journal of the Care of the Injured 365(4):S24-S29, Nov. 2005.
Johnson, F.A., "Characterization of the Block Structure and Molecular Weight of Sodium Alginates," Journal of Pharmaceutical Pharmacology 49(7):639-643, Jul. 1997.
Kumar, M.N.V.R., et al., "Chitosan Chemistry and Pharmaceutical Perspectives," Chemical Reviews 104(12):6017-6084, Dec. 2004.
Lacroix, D., and P.J. Prendergast, "A Mechano-Regulation Model for Tissue Differentiation During Fracture Healing: Analysis of Gap Size and Loading," Journal of Biomechanics 35(9):1163-1171, Sep. 2002.

(56) References Cited

OTHER PUBLICATIONS

Langer, R., and D.A. Tirrell, "Designing Materials for Biology and Medicine," Nature 428(6982):487-492, Apr. 2004.

Leach, J.B., "Tissue-Engineered Peripheral Nerve," in M. Akay (ed.), "Wiley Encyclopedia of Biomedical Engineering," Wiley, Hoboken, N.J., 2006, pp. 3568-3578.

Lee, D.A., et al., "Expansion of Chondrocytes for Tissue Engineering in Alginate Beads Enhances Chondrocytic Phenotype Compared to Conventional Monolayer Techniques," Acta Orthopaedica Scandinavia 74(1):6-15, Feb. 2003.

Leung, M., et al., "Nanofiber-Based in Vitro System for High Myogenic Differentiation of Human Embryonic Stem Cells," Biomacromolecules 14(12):4207-4216, Dec. 2013.

Li, D., et al. "Nanofibers of Conjugated Polymers Prepared by Electrospinning With a Two-Capillary Spinneret," Advanced Materials 16(22):2062-2066, Nov. 2004.

Li, W.-J., et al., "Electrospun Nanofibrous Structure: A Novel Scaffold for Tissue Engineering," Journal of Biomedical Materials Research 60(4):613-621, Jun. 2002.

Li, Z., and M. Zhang, "Chitosan-Alginate as Scaffolding Material for Cartilage Tissue Engineering," Journal of Biomedical Materials Research 75A(2):485-493, Nov. 2005.

Lin, H.-R., and Y.-J. Yeh, "Porous Alginate/Hydroxyapatite Composite Scaffolds for Bone Tissue Engineering: Preparation, Characterization, and In Vitro Studies," Journal of Biomedical Materials Research 71B(1):52-65, Oct. 2004.

Lutolf, M.P., and J.A. Hubbell, "Synthetic Biomaterials as Instructive Extracellular Microenvironments for Morphogenesis in Tissue Engineering," Nature Biotechnology 23(1):47-55, Jan. 2005.

Maher, S.A., and P.J. Prendergast, "Discriminating the Loosening Behaviour of Cemented Hip Prostheses Using Measurements of Migration and Inducible Displacement," Journal of Biomechanics 35(2):257-265, Feb. 2002.

Mallein-Gerin, F., et al., "Proteoglycan and Collagen Synthesis Are Correlated With Action Organization in Dedifferentiating Chondrocytes," European Journal of Cell Biology 56(2):364-373, Dec. 1991.

Marijnissen, W.J.C.M., et al., "Tissue-Engineered Cartilage Using Serially Passaged Articular Chondrocytes. Chondrocytes in Alginate, Combined In Vivo With a Synthetic (E210) or Biologic Biodegradable Carrier (DBM)," Biomaterials 21(6):571-580, Mar. 2000.

Masuda, K., et al., "A Novel Two-Step Method for the Formation of Tissue-Engineered Cartilage by Mature Bovine Chondrocytes: The Alginate-Recovered-Chondrocyte (ARC) Method," Journal of Orthopaedic Research 21:139-148, 2003.

Matsuda, A., et al., "Preparation of Chitosan Nanofiber Tube by Electrospinning," Journal of Nanoscience and Nanotechnology 7(3):852-855, Mar. 2007.

McKee, M.G., et al., "Phospholipid Nonwoven Electrospun Membranes," Science 311(5759):353-355, Jan. 2006.

International Search Report and Written Opinion mailed Nov. 21, 2007, issued in corresponding International Application No. PCT/US2007/065388, filed Mar. 28, 2007, 10 pages.

Jin, H.-J., et al., "Electrospinning Bombyx Mori Silk with Poly(Ethylene Oxide)," Biomacromolecules, 3(6):1233-1239, Aug. 28, 2002.

Lu, J.-W. et al., "Electrospinning of Sodium Alginate with Poly(Ethylene Oxide)," Polymer, 47(23):8026-8031, Oct. 4, 2006.

Safi, S., et al., "Study of Electrospinning of Sodium Alginate, Blended Solutions of Sodium Alginate/Poly(Vinyl Alcohol) and Sodium Alginate/Poly(Ethylene Oxide)," Journal of Applied Polymer Science, 104(5):3245-3255, Mar. 8, 2007.

\* cited by examiner

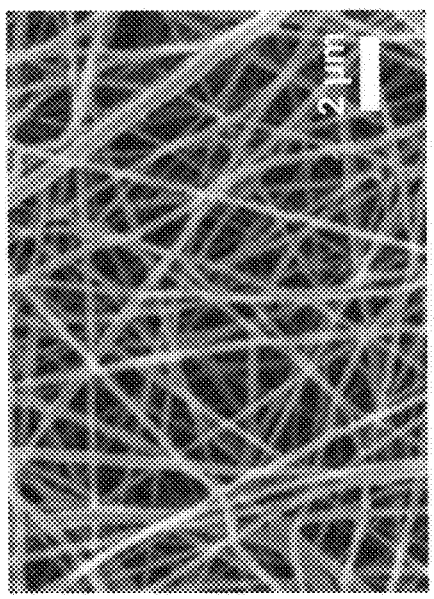
*Fig. 2A.* 40:60
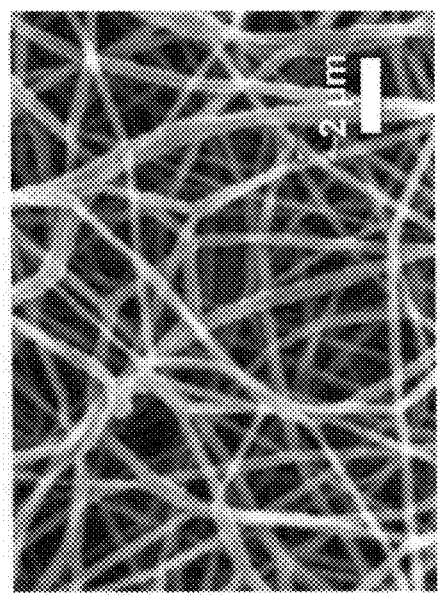
*Fig. 2B.* 60:40
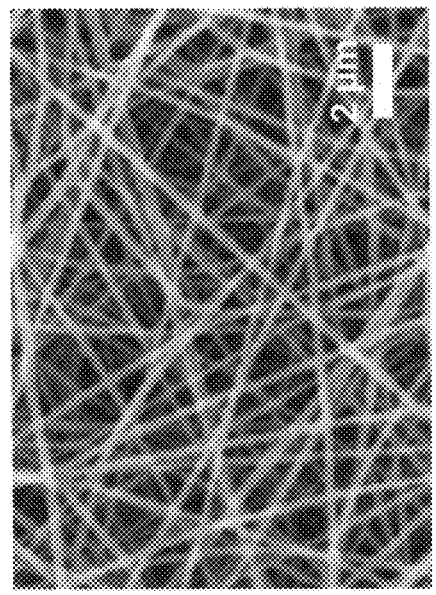
*Fig. 2C.* 70:30
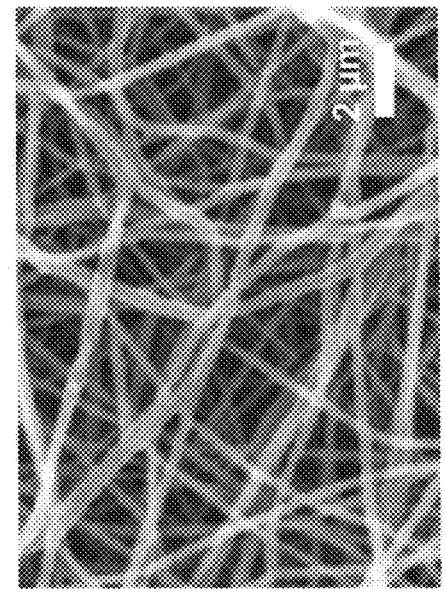
*Fig. 2D.* 80:20

NANOFIBROUS CONDUITS FOR NERVE REGENERATION

STATEMENT OF GOVERNMENT LICENSE RIGHTS

This invention was made with Government support under Contract No. NSF-EEC 9529161 awarded by the National Science Foundation. The Government has certain rights in the invention.

BACKGROUND OF THE INVENTION

Development of polymeric nanofibers is of great scientific and technological interest because of their wide-range applications in biomedicine and biotechnology. Particularly, composite nanofibers derived from natural and synthetic polymers, capitalizing on the favorable biological properties of the natural polymer and mechanical strength of the synthetic polymer, represents a major advancement in tissue engineering and regenerative medicine. However, the development of well-blended natural-synthetic composite polymers remains a great challenge due to the poor miscibility of the component polymers, where natural polymers are generally soluble in aqueous and polar solvents, but most synthetic polymers are not. Poorly blended polymeric nanofibers exhibit weak mechanical strength and uncontrollable material properties as a result of inhomogeneity.

Large-gap nerve damage that cannot be directly repaired with sutures has typically been treated using nerve autografts, but this technique suffers from donor site morbidity, inadequate return of function, aberrant regeneration, and shortage of donor tissue. An alternative approach is to use a nerve guide conduit serving both to promote nerve regeneration and to provide a pathway for nerve outgrowth. A number of polymeric nanofibers, including poly(caprolactone) (PCL), poly(lactic acid) (PLLA), poly(lactic-co-glycolic acid) (PLGA), collagen, and chitosan, are emerging as promising candidates for nerve repair. While the advances in nerve regeneration are encouraging, few of current nerve guide materials succeed in showing structural stability and pliability in physiological environments.

Common problems confronted in application of artificial nerve guides as a result of unsatisfactory mechanical or biological properties of nerve conduits include structural collapse, material swelling, early resorption, and release of cytotoxic degradation products.

Despite the advances in materials for nerve regeneration, a need exist for nerve regeneration conduits having biocompatibility and mechanical strength, and that support nerve growth. The present invention seeks to fulfill this need and provides further related advantages.

SUMMARY OF THE INVENTION

The present invention provides a nanofiber comprises of chitosan and poly(caprolactone), a fibrous conduit for promoting regeneration of a severed nerve made from the fiber, methods for making the conduit, and methods for using the conduit for nerve regeneration.

In one aspect, the invention provides nanofibers comprising chitosan and poly(caprolactone). The chitosan-poly(caprolactone) fibers can be prepared by electrospinning a solution that includes chitosan and poly(caprolactone). The chitosan-poly(caprolactone) fibers include from about 10 to about 80 percent by weight chitosan and from about 90 to about 20 percent by weight poly(caprolactone) based on the total weight of the fiber. The chitosan-poly(caprolactone) fibers can have a diameter of from about 50 to about 2000 nm.

In another aspect, the invention provides a conduit for promoting neural regeneration across the gap between severed ends of a nerve. In one embodiment, the invention provides a fibrous conduit for promoting regeneration of a severed nerve, the conduit having a first end for coapting the conduit to a first end of a severed nerve and a second end for coapting the conduit to a second end of the severed nerve. The conduit comprises chitosan-poly(caprolactone) fibers.

The conduit has a length sufficient to bridge the gap between severed nerve endings. In certain embodiments, the conduit has a length from about 0.1 to about 100 cm. The conduit has an inner diameter sufficient to receive severed nerve endings. In certain embodiments, the conduit has an inner diameter from about 1 to about 10 mm. The conduit thickness can be varied depending on the desired application. In certain embodiments, the conduit has a thickness from about 0.1 to about 1.0 mm.

The conduit has both mechanical strength and pliability. In certain embodiments, the conduit has a breaking strength from about 0.5 to about 100 MPa in the dry state. In certain embodiments, the conduit has a breaking strength from about 0.1 to about 50 MPa in the wet state. In certain embodiments, the conduit has a compressive strength from about 0.1 to about 20 N at 10% compression in the wet state. In certain embodiments, the conduit has a compressive strength from about 1 to about 50 N at 50% compression in the wet state. In certain embodiments, the conduit has a modulus from about 0.05 to about 1000 MPa in the dry state. In certain embodiments, the conduit has a modulus from about 0.5 to about 200 MPa in the wet state.

In another aspect of the invention, methods for making the conduit are provided. In one embodiment, the method is an electrospinning method and includes generating an electrostatic field between a first electrode and a second electrode; and electrospinning a solution of chitosan and poly(caprolactone) onto a rotating cylindrical collector intermediate the first and second electrodes to provide a fibrous conduit comprising chitosan-poly(caprolactone) fibers.

The solution from which the chitosan-poly(caprolactone) fibers are spun includes from about 10 to about 90 percent by weight chitosan and from about 20 to about 80 percent by weight poly(caprolactone) based on the total weight of the solution.

In a further aspect, the invention provides methods for promoting regeneration of a severed nerve using the conduit. In the method, the proximal end of a severed nerve is coapted to the first end of the conduit and the distal end of the severed nerve is coapted to the second end of the conduit. In one embodiment, coapting the first end of the conduit to the proximal end of the severed nerve comprises suturing the first end of the conduit to the proximal end of the severed nerve. In one embodiment, coapting the second end of the conduit to the distal end of the severed nerve comprises suturing the second end of the conduit to the distal end of the severed nerve.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1B illustrates the conduit in nerve regeneration.

FIGS. 2A-2D are SEM images of representative chitosan-PCL nanofibers of the invention prepared with different ratios of chitosan to PCL (chitosan:PCL=40:60, 60:40, 70:30, and 80:20) showing the spinnability of the solution in a wide range of chitosan-to-PCL ratios to produce bead-free nanofibers.

DETAILED DESCRIPTION OF THE INVENTION

Figure 1A:
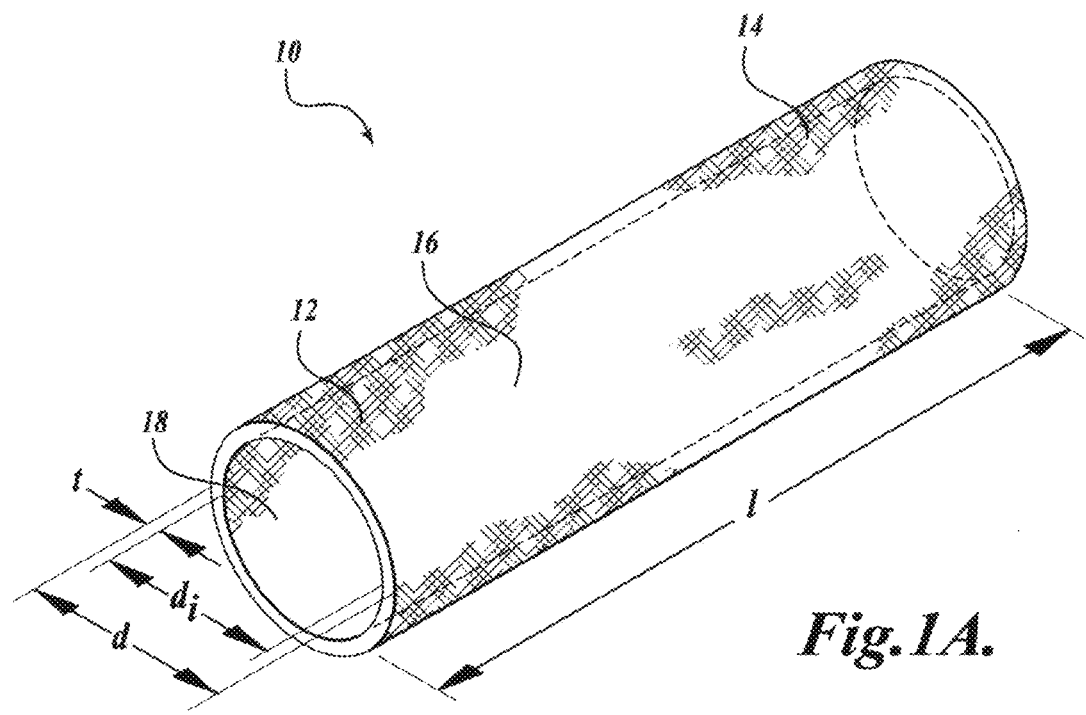
FIGS. 1A and 1B are illustrations of a representative nanofiber conduit of the invention.

The present invention provides a nanofiber comprises of chitosan and poly(caprolactone), a fibrous conduit for promoting regeneration of a severed nerve made from the fiber, methods for making the conduit, and methods for using the conduit for nerve regeneration.

In one aspect, the present invention provides a natural/synthetic polymeric nanofiber comprised of well-blended chitosan and poly(caprolactone) (PCL). The nanofiber combines the technological advances in biocompatible polymers and nanotechnology to produce nanofibrous matrices with significantly improved mechanical and biological properties. Chitosan, a biodegradable, nonantigenic, and biocompatible natural polymer, bears the proxy structure of glycosaminoglycan (GAG), a major component of the native extracellular matrix (ECM). GAGs of the ECM are known to support enhanced cell attachment and proliferation and improve the material's cellular and tissue biocompatibilities. However, chitosan is mechanically weak, and alone it is unable to retain its structural integrity, swelling in aqueous environments. The complementary polymer of the nanofibers of the invention is PCL, which is commonly found in tissue engineering applications due to its structural and mechanical stability. PCL has limited cell affinity due primarily to its hydrophobicity and lack of surface cell recognition sites. The well-blended chitosan-PCL nanofibrous matrix that integrates the favorable biological properties of chitosan and mechanical properties of PCL significantly improves material properties, while providing a stable, nurturing environment for a broad array of biomedical applications.

Thus, in one aspect, the invention provides nanofibers useful for making nerve regeneration conduits are provided. The nanofibers comprise chitosan and poly(caprolactone). Suitable nanofibers comprise from about 10 to about 80 percent by weight chitosan and from about 90 to about 20 percent by weight poly(caprolactone). In one embodiment, the chitosan-poly(caprolactone) fibers comprise about 10 percent by weight chitosan and about 90 percent by weight poly(caprolactone). In another embodiment, the chitosan-poly(caprolactone) fibers comprise about 20 percent by weight chitosan and about 80 percent by weight poly(caprolactone). In another embodiment, the chitosan-poly(caprolactone) fibers comprise about 30 percent by weight chitosan and about 70 percent by weight poly(caprolactone). In another embodiment, the chitosan-poly(caprolactone) fibers comprise about 40 percent by weight chitosan and about 60 percent by weight poly(caprolactone). In another embodiment, the chitosan-poly(caprolactone) fibers comprise about 50 percent by weight chitosan and about 50 percent by weight poly(caprolactone). In another embodiment, the chitosan-poly(caprolactone) fibers comprise about 60 percent by weight chitosan and about 40 percent by weight poly(caprolactone). In another embodiment, the chitosan-poly(caprolactone) fibers comprise about 70 percent by weight chitosan and about 30 percent by weight poly(caprolactone). In another embodiment, the chitosan-poly(caprolactone) fibers comprise about 80 percent by weight chitosan and about 20 percent by weight poly(caprolactone).

The chitosan-poly(caprolactone) fibers can have a diameter of from about 50 to about 2000 nm. In one embodiment, the chitosan-poly(caprolactone) fibers have a diameter of from about 150 to about 600 nm.

The chitosan-poly(caprolactone) fibers can be prepared by electrospinning a solution that includes chitosan and poly(caprolactone). Chitosan suitable for use in making the fiber has an average molecular weight greater than about 10 kDa. In one embodiment, the chitosan has an average molecular weight of from about 50 to about 1000 kDa. In one embodiment, chitosan suitable for use in making the fiber has a degree of deacetylation between 75 and 85%. Poly(caprolactone) suitable for use in making the fiber has an average molecular weight greater than about 20 kDa. In one embodiment, the PCL has an average molecular weight of from about 20 to about 100 kDa. In one embodiment, the PCL has an average molecular weight of from about 70 to about 90 kDa.

Figure 3A:
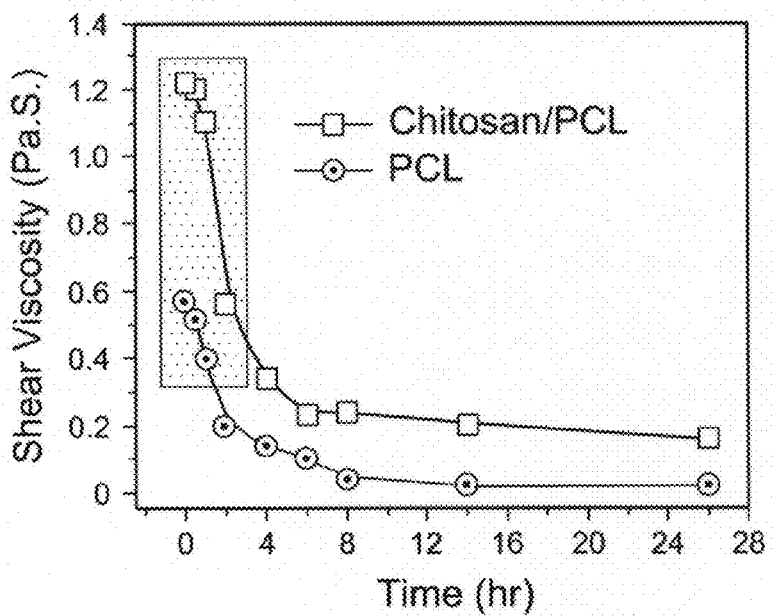
FIG. 3A is a graph comparing the spinnability of chitosan-PCL (chitosan:PCL=40:60) and PCL solutions (shear viscosity, PaS) as a function of solution storage time at room temperature, showing that solution viscosity decreases over time after solution preparation and there is a time window beyond which no fibrous structure can be obtained.

Nanofibrous structures generated by electrospinning can exhibit diverse fiber sizes, uniformity, integrity, and miscibility, depending on processing conditions, component ratios, and solvents used. In one embodiment, the nanofibers of the invention are prepared from mixtures of chitosan in trifluoroacetic acid (5 wt %) and PCL in trifluoroethanol (10 wt %) at a component ratio range between 40:60 and 80:20 (chitosan:PCL) to provide solid, bead-free, uniform chitosan-PCL nanofibers. SEM micrographs of representative chitosan-PCL nanofibers (chitosan:PCL=40:60, 60:40, 70:30, and 80:20) are illustrated in FIGS. 2A-2D). Varying these parameters and processing conditions provides flexibility to fine tune structural, mechanical, and biological properties suitable for specific applications. For nerve guide conduits, a blend solution ratio of 40:60 (chitosan:PCL) (See FIG. 2A) provided suitable fibrous structural and mechanical properties, and this particular composition was used in subsequent experimentation and exemplifies representative compositions suitable for the nerve guide conduits of the invention. Continuous nanofiber production was limited by acidic hydrolysis of PCL by TFA over time, requiring component mixing shortly prior to the electrospinning process. This is illustrated by the shear viscosity of chitosan-PCL solution (40:60) as a function of storage time after mixing chitosan solution with PCL solution at room temperature (see FIG. 3A), and the morphology of electrospun products generated at different time points (see FIG. 3B). The grey box in FIG. 3A indicates the time window in which the solution is spinnable producing bead-free, uniform nanofibrous structures.

The physical properties and biodegradation rate of polymer blends are strongly dependent upon their crystallinity, where phase inhomogeneities generally weaken the mechanical strengths of materials. This is particularly true when the material's size dimension is reduced to the nanoscale. Miscible polymer blends can produce new materials with designated properties superseding those of their constituents. However, well-established miscible polymer blends are rare, and immiscible blend components are frequently identified by porous or phase segregated structures. Tunneling electron microscopy (TEM), X-ray diffraction, and differential scanning calorimetry (DSC) thermograms were employed to assess the phase miscibility of the chitosan-PCL nanofibers of the invention produced by electrospinning.

No component partitioning or porous structures were observed by TEM in chitosan-PCL nanofibers (FIG. 4B), indicating good phase miscibility of the blend polymer. The diffraction pattern (FIG. 4C) of the chitosan-PCL nanofibers acquired with wide angle X-ray scattering (WAXS) shows that characteristic diffraction peaks of PCL ($21.5°$ and $23.6°$) was significantly weakened when the chitosan content in the nanofiber was increased to above 20 wt %, suggesting decreased crystallinity of PCL with addition of chitosan and strong miscibility of chitosan and PCL. The lower crystallinity of a component material indicates better miscibility of blended nanofibers. Differential scanning calorimetry (DSC) thermograms of the prepared chitosan-PCL samples show shifts in glass transition and endothermic temperatures, but no additional peaks compared to the thermogram of a chitosan and PCL powder mixture (see FIG. 5A). This indicates the formation of a new material phase (chitosan-PCL) and absence of additional phases, which further confirms the advantageous miscibility of chitosan and PCL.

Figure 5A:
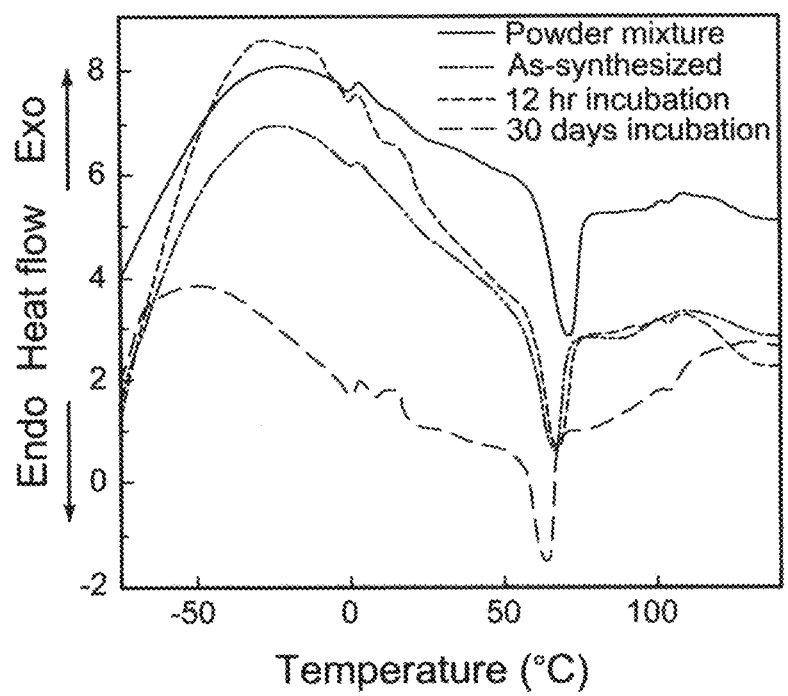
FIG. 5A compares DSC thermograms of representative chitosan-PCL nanofibers (chitosan:PCL=40:60) of the invention prior to (as-synthesized) incubating the fibers with a lysozyme-PBS mixture for 12 hr and 30 days. A physical mixture of chitosan and PCL (chitosan:PCL=40:60) is shown as reference (powder mixture).
Figure 5B:
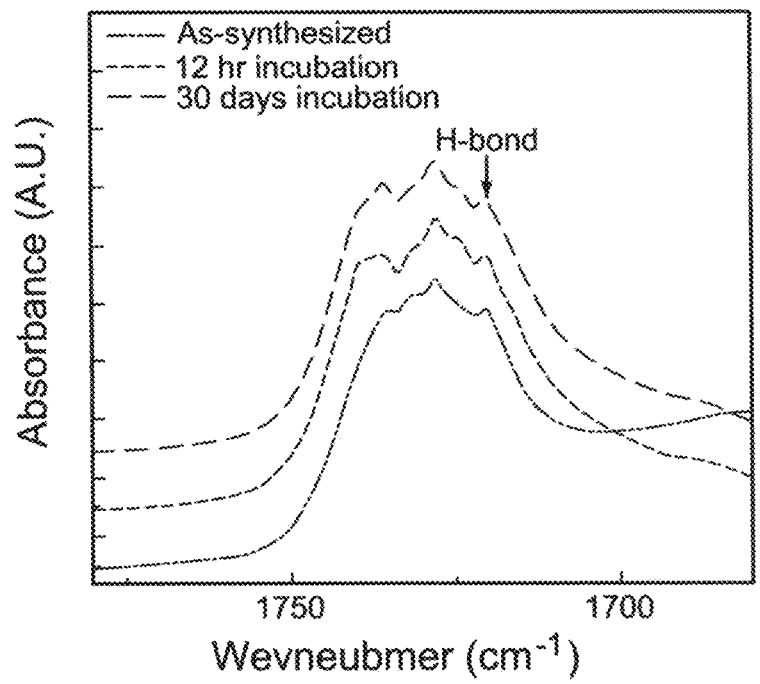
FIG. 5B compares FTIR spectra of representative chitosan-PCL nanofibers (chitosan:PCL=40:60) of the invention prior to (as-synthesized) incubating the fibers with a lysozyme-PBS mixture for 12 hr and 30 days.

The demonstration of advantageous miscibility between chitosan and PCL in the electrospun nanofibers, which is otherwise difficult to achieve by alternative techniques such as film casting, freeze-drying, or melt blending, may be attributed to intermolecular hydrogen bonding between PCL carbonyl groups and chitosan amine groups (see FIG. 5B) and rapid solidification of the mixture solution of chitosan and PCL achieved by electrospinning preventing PCL aggregation.

Nanofibrous constructs are required to maintain their structural and mechanical integrity for biomedical applications such as tissue regeneration and regenerative medicine. As the body's aqueous environment and high lysozyme content are considered to be the primary sources of polymer degradation, chitosan-PCL fibrous matrices were tested in vitro at 37° C. in a lysozyme-rich PBS solution for up to one month. No discernable changes to the structural integrity and chemistry of the nanofiber were identified by SEM/TEM (see FIGS. 4D and 4E), DSC, and Fourier transform infrared spectroscopy (FTIR) analyses (see FIGS. 5A and 5B) indicating that the PCL-chitosan nanofiber has a slow degradation rate and is capable of retaining its integrity for prolonged time.

The cellular compatibility of chitosan-PCL nanofibers with neuronal cells for nerve regeneration was assessed by incubation with Schwann cells and PC12 cells. Schwann and PC12 cells are used in nerve regeneration to support and direct neurite processes, respectively. The cells were also cultured on PCL nanofibers and chitosan-PCL films for comparison.

Figure 6A:
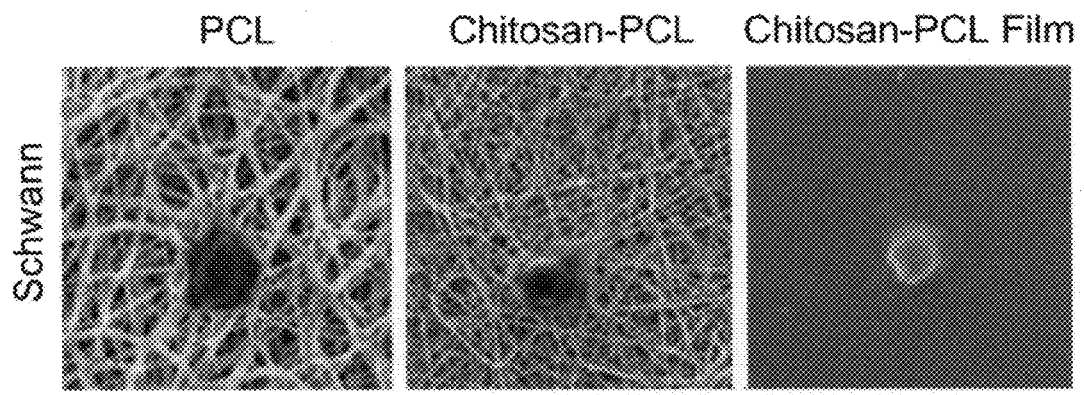
FIGS. 6A and 6B are SEM images comparing Schwann (6A, 1 day) and PC12 (6B, 7 days) cell adherence and growth on a PCL fibrous structure (PCL) and representative chitosan-PCL structures of the invention (chitosan:PCL=40:60) (Chitosan-PCL and Chitosan-PCL Film).

Schwann cells exhibited the most significant spreading on the chitosan-PCL fibers as indicated by the large, polar cell body, while the Schwann cells on the PCL nanofibers and chitosan-PCL film had smaller, spherical cell morphologies (FIG. 6A). The number of Schwann cells on all the materials increased similarly with time (FIG. 6D), indicating no significant difference in Schwann cell attachment and proliferation among the tested materials.

Figure 6B:
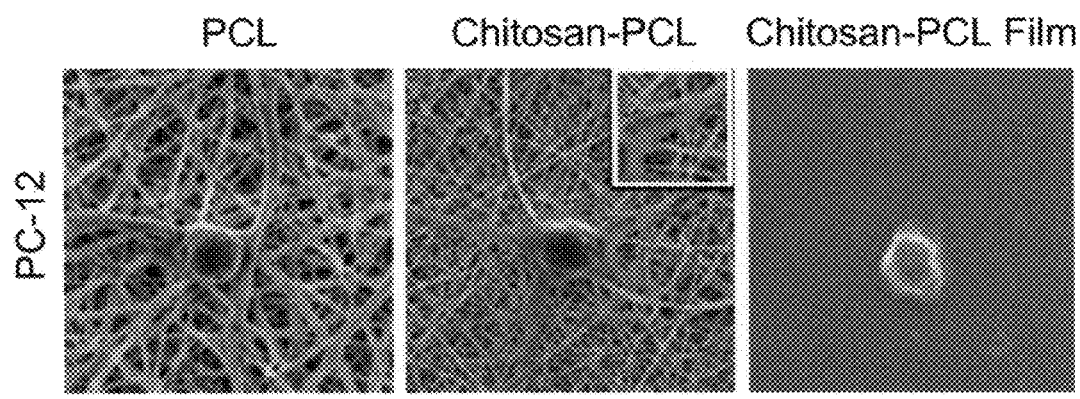

Similarly, PC12 cells exhibited the most significant spreading on chitosan-PCL nanofibers with more extended neuritis compared to those on the control materials which exhibited smaller and spherical cell bodies (FIG. 6B). The neurite extension was better observed by immunostaining PC12 cells with antibody against nerve growth factor (NGF) receptor. Confocal fluorescence images showed a significantly higher degree of neurite expansion of PC12 cells on the chitosan-PCL nanofibers than on the control materials (FIG. 6C), consistent with the SEM observation (FIG. 6A). No apparent increase in PC12 cell number was observed on either substrate over time (FIG. 6E), as expected, because PC12 cells in the presence of NGF are subjected to differentiation and do not proliferate. More PC12 cells were attached to chitosan-PCL nanofiber and film substrates than on PCL nanofibers at day 1, indicating good cell adherence to chitosan-PCL materials, supporting the hypothesis that more active cell binding sites presented by chitosan would facilitate cell attachment. It is noted that after continued incubation and replacement of the cell media through a period of 5 days, the number of PC12 cells on the chitosan-PCL nanofibers remained about the same while the numbers of the cells on chitosan-PCL films was reduced, indicating that the cells were more strongly adhered on nanofibrous structures. Overall, the chitosan-PCL nanofibers maintained the highest cell number throughout the 5-day study, exhibiting the best initial cell attachment and the strongest cell-material interaction.

In another aspect, the invention provides a conduit useful for promoting neural regeneration across the gap between severed ends of a nerve. A representative conduit of the invention is illustrated in FIG. 1A. Referring to FIG. 1A, fibrous conduit 10 has first end 12 and second end 14. The conduit is a hollow fibrous conduit (i.e., a tubular structure) having outer surface 16, inner surface 18, length l, diameter d, internal diameter $d_i$, and thickness t.

Figure 1B:
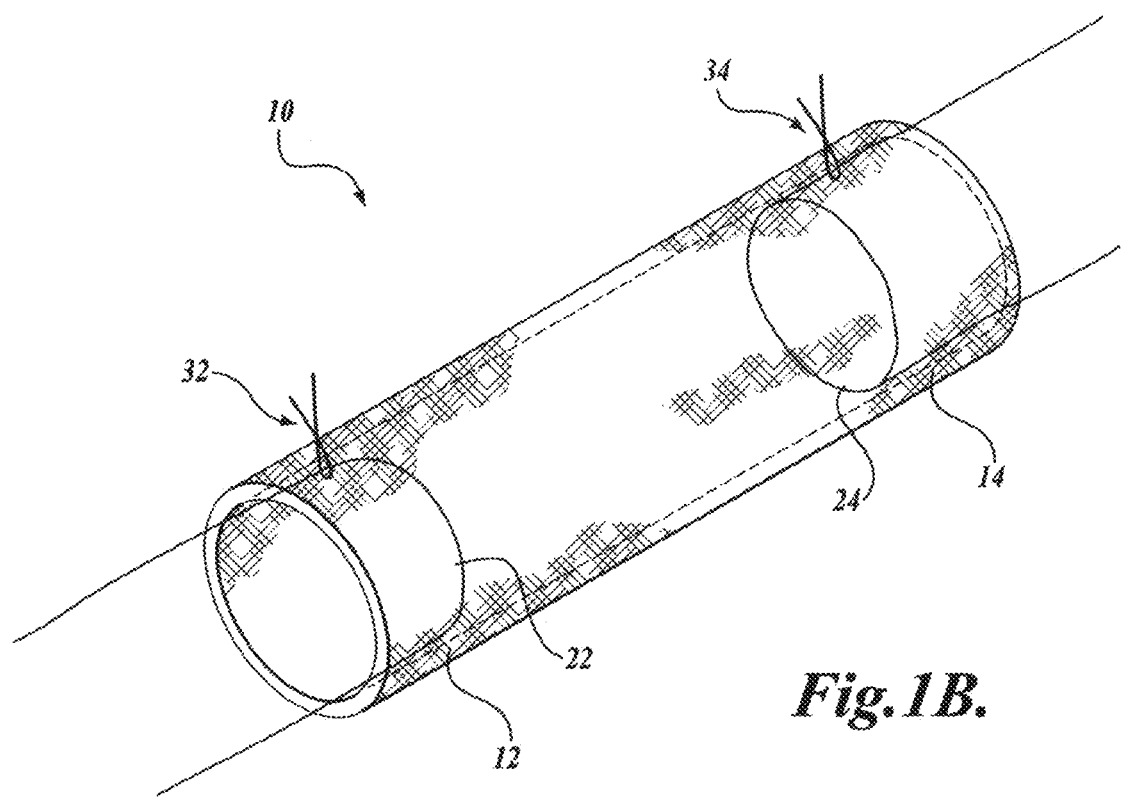

The conduit is useful for promoting neural regeneration across the gap between severed ends of a nerve as illustrated in FIG. 1B. Referring to FIG. 1B, conduit 10 has first end 12 for coapting (i.e., securing) the conduit to the first end of a severed nerve 22 and second end 14 for coapting the conduit to the second end of the severed nerve 24. The conduit can be coapted to the severed nerve ends by sutures (32 and 34).

The conduit is made from chitosan-poly(caprolactone) fibers of the invention. As used herein, the term "chitosan-poly(caprolactone) fibers" or "chitosan-PCL fibers" refers to a fiber prepared from a blend of chitosan and poly(caprolactone) by, for example, electrospinning. The fibers can also be prepared by wet spinning and melt spinning methods. These methods generate fibers having diameters ranging from a few microns to several hundred microns. The chitosan-poly(caprolactone) fibers can be prepared by electrospinning a solution that includes chitosan and poly(caprolactone). The chitosan-poly(caprolactone) fibers include from about 10 to about 80 percent by weight chitosan and from about 90 to about 20 percent by weight poly(caprolactone) based on the total weight of the fiber. The conduit can be fabricated by electrospinning the fiber onto a rotating cylindrical collector. A method for preparing representative conduits of the invention is described in Example 1.

The conduit has a length sufficient to bridge the gap between severed nerve endings. In certain embodiments, the conduit has a length from about 0.1 to about 100 cm. The conduit has an inner diameter sufficient to receive severed nerve endings. In certain embodiments, the conduit has an inner diameter from about 1 to about 10 mm. The conduit thickness can be varied depending on the desired application. In certain embodiments, the conduit has a thickness from about 0.1 to about 1.0 mm.

As described below, the conduit has both mechanical strength and pliability. In certain embodiments, the conduit has a breaking strength from about 0.5 to about 100 MPa in the dry state. In certain embodiments, the conduit has a breaking strength from about 0.1 to about 50 MPa in the wet state. In certain embodiments, the conduit has a compressive strength from about 0.1 to about 20 N at 10% compression in the wet state. In certain embodiments, the conduit has a compressive strength from about 1 to about 50 N at 50% compression in the wet state. In certain embodiments, the conduit has a modulus from about 0.05 to about 1000 MPa in the dry state. In certain embodiments, the conduit has a modulus from about 0.5 to about 200 MPa in the wet state.

To enhance nerve regeneration, the conduit can include one or more neurotrophic agents. Representative neurotrophic agents include FK506, aFGF, PFGF, 4-methylcatechol, NGF, BDNF, CNTF, MNGF, NT-3, GDNF, NT-4/5, CM101, inosine, spermine, spermidine, HSP-27, IGF-I, IGF-II, PDGF, ARIA, LIF, VIP, GGF, IL-1, and MS-430.

Nerve conduits were constructed by electrospinning the solution of chitosan and PCL onto a stainless steel rod collector of set diameter (e.g., from about 0.8 to about 8 mm). Variations in length and diameter of the collector produced nanofibrous conduits with thicknesses of 0.2-1.0 mm, inner diameters of 1-5 mm, and lengths of 5-15 cm.

Nerve conduits are required to be structurally stable while retaining sufficient mechanical strength and pliability for nerve regeneration. Conduits that are too rigid can break and induce scarring of neighboring tissue, while weak materials can be easily compressed, occluding the nerve growth pathway. Mechanical properties of the conduit were assessed by tensile and compressive tests. The breaking strengths for the chitosan-PCL conduit was found to be 5.3±0.5 (dry) and 2.9±1.3 MPa (wet) (FIG. 7A) and Young's modulus was found to be 110±10 MPa and 103±1.2 MPa at dry and wet states, respectively (FIG. 6B). For comparison, two control nerve guides were also tested: a widely studied biomaterial for nerve guides, PLGA, prepared by the same electrospinning process, and a commercially available collagen conduit (Integra LifeSciences Corporation, Plainsboro, N.J.). Both the PLGA and collagen conduits were much more susceptible to wetting than the chitosan-PCL conduit, and exhibited markedly lower moduli when wet. All tested materials retained relatively similar breaking strengths. Pliability of the nanofibrous conduit was assessed with compressive load applied perpendicularly to the length of the tube. Compressive strength of the wet chitosan-PCL conduit was 0.5 and 3.5 N at 10% and 50% compression, respectively (FIGS. 7C and 7D, respectively). Wet PLGA and collagen nanofibrous conduits showed much lower compressive strengths with increasing deformation. Chitosan-PCL cast tubes of the same thickness as chitosan-PCL nanofibrous conduits were tested to illustrate the difference in applicability between bulk and nanofibrous preparations. The cast tubes fractured after being compressed over 10% while nanofibrous conduits exhibited elastic deformation at elevated compression.

In assessing mechanical properties of nerve conduits, the data obtained with wet conduits more closely reflect in vitro and in vivo conditions compared to mechanical performance of dry materials. These differences can be substantial (see FIGS. 7A-7D). It is not surprising that a nerve guide that had been previously identified to be mechanically competent in dry state failed in service due to materials swelling, early resorption, or degradation. The nanofibrous matrix of the invention has high mechanical and chemical stabilities in aqueous environments.

Figure 7A:
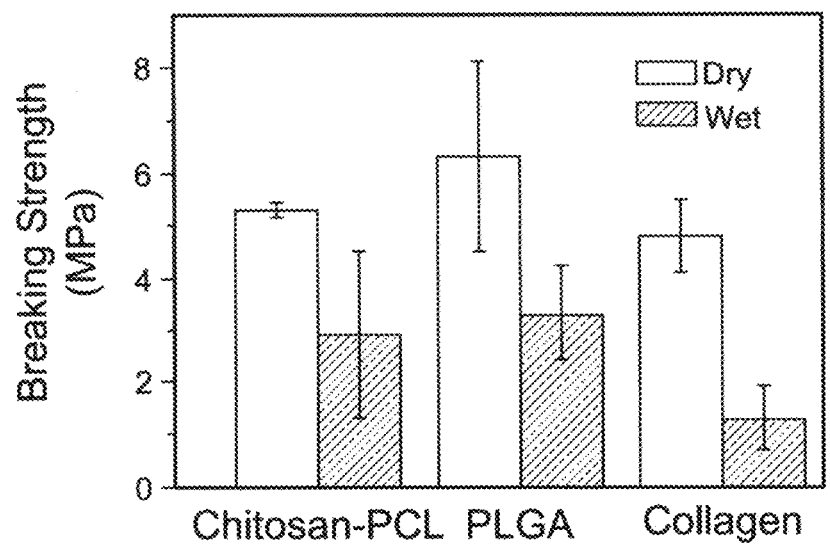
FIG. 7A is a graph comparing dry and wet breaking strength (MPa) for representative chitosan-PCL nanofibrous conduits of the invention (Chitosan-PCL) (chitosan:PCL=40:60) to PLGA and Collagen conduits.
Figure 7B:
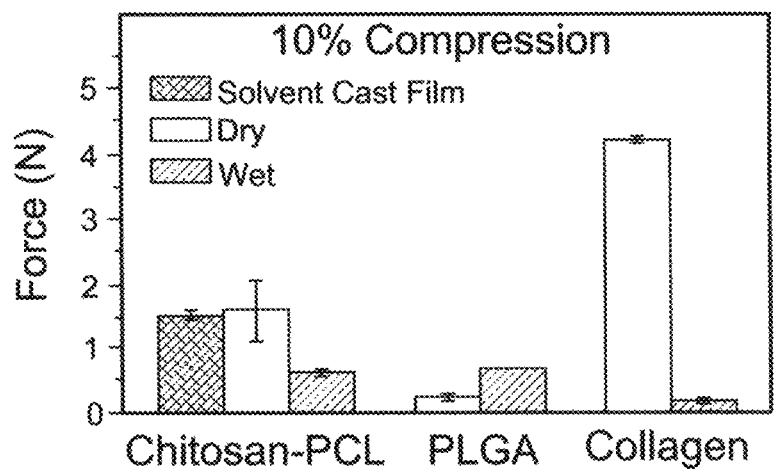
FIG. 7B is a graph comparing dry and wet Young's modulus (MPa) for representative chitosan-PCL nanofibrous conduits of the invention (Chitosan-PCL) (chitosan:PCL=40:60) to PLGA and Collagen conduits.
Figure 7C:
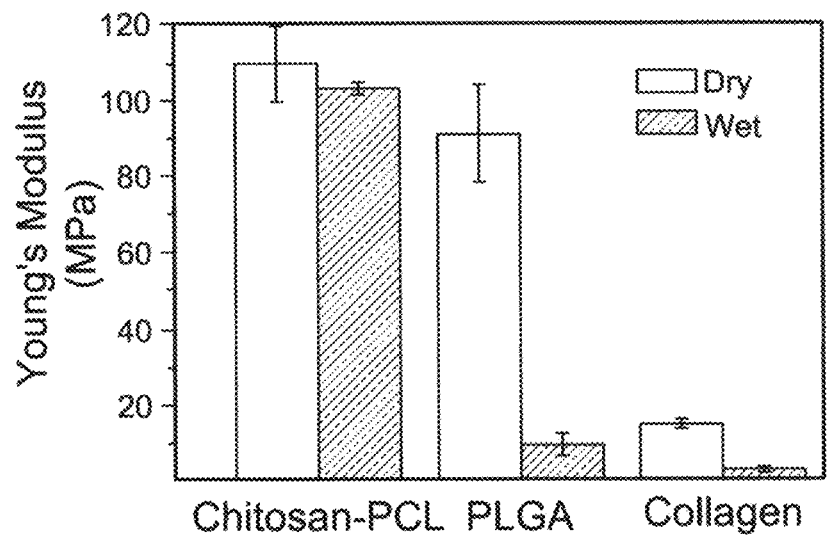
FIG. 7C is a graph comparing solvent cast film, dry, and wet 10% compression (force, N) for representative chitosan-PCL nanofibrous conduits of the invention (Chitosan-PCL) (chitosan:PCL=40:60) to PLGA and Collagen nanofibrous conduits. The solvent cast chitosan-PCL conduit illustrates the superior mechanical properties of the nanofibrous structure.
Figure 7D:
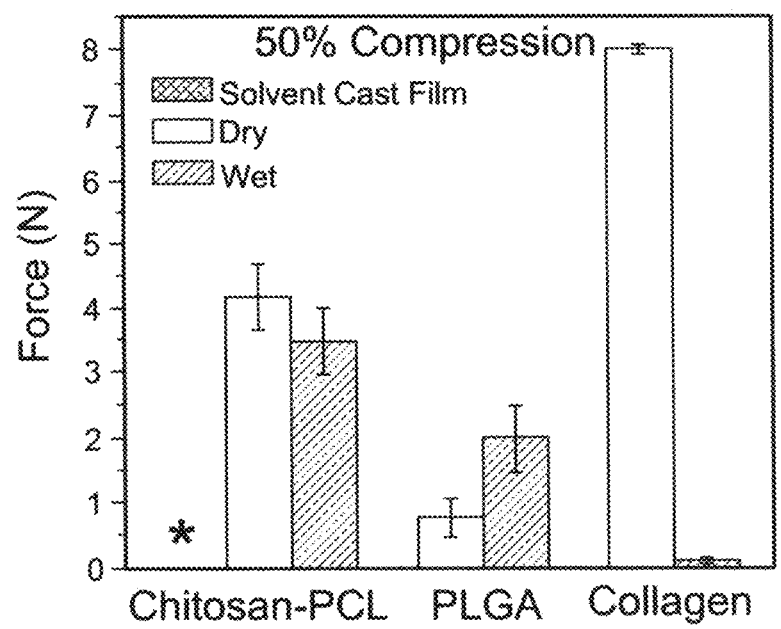
FIG. 7D is a graph comparing solvent cast film, dry, and wet 50% compression (force, N) for representative chitosan-PCL nanofibrous conduits of the invention (Chitosan-PCL) (chitosan:PCL=40:60) to PLGA and Collagen nanofibrous conduits. The solvent cast chitosan-PCL conduit illustrates the superior mechanical properties of the nanofibrous structure. *Compressive testing of the solvent cast tube at 50% compression resulted in premature sample fracture.

The interaction of chitosan-PCL conduits with neuronal cells and cell-cell interaction were assessed in vitro by co-culturing Schwann cells with PC12 cells. Green fluorescence protein (GFP) transfected Schwann cells seeded onto the conduit were allowed to attach and spread for 1 week prior to co-cultured with PC12 cells. After 11 days of co-culture in NGF-rich media, all cells were fixed and PC12 cells were immunochemically stained. Confocal microscopy identified two cell layers stained in green (Schwann cells) and red (PC12 cells) covering the inner and outer surfaces of the nerve conduits (FIG. 7E), signifying that both Schwann and PC12 cells attached and proliferated well on the conduit. Samples recovered, fixed and imaged by SEM showed extended neurite growth of the seeded cells, demonstrating that PC12 cells were functional and Schwann cells promoted the axon growth of PC12 cells (FIG. 7F). These findings indicate that the bicomponent conduit retained sufficient cellular compatibility for the preservation of neural functionality and growth. Referring to FIG. 7F, cells on the chitosan-PCL were densely populated and the cell interactions with underlying nanofibers cannot be readily observed. To better reveal the cell-material interactions, Schwann and PC12 cells were seeded on chitosan-PCL nanofibers at a lower concentration and co-cultured for a shorter period of time (7 days) for unobstructed observation at high SEM magnification. See FIGS. 8A (lower magnification) and 8B (higher magnification). Referring to FIGS. 8A and 8B, Schwann and PC12 cells are seen to adhere well to the chitosan-PCL nanofibers and exhibit their characteristic spindle and round morphologies. These results indicate that the bicomponent nanofibers retain sufficient cellular compatibility for the preservation of neural functionality and growth.

In a further aspect, the invention provides methods for promoting regeneration of a severed nerve using the conduit. In the method, the proximal end of a severed nerve is coapted to the first end of the conduit and the distal end of the severed nerve is coapted to the second end of the conduit. In one embodiment, coapting the first end of the conduit to the proximal end of the severed nerve comprises suturing the first end of the conduit to the proximal end of the severed nerve. In one embodiment, coapting the second end of the conduit to the distal end of the severed nerve comprises suturing the second end of the conduit to the distal end of the severed nerve.

Representative chitosan-PCL nanofibrous conduits of the invention were evaluated in vivo for nerve regeneration in a rat sciatic defect model as described in Example 9. Nerve conduits were implanted in a critical-size sciatic nerve defect in rats for one month. Images of silver-stained cross sections of native (left) and new nerves formed in a representative chitosan-PCL (chitosan:PCL=40:60) nanofibrous conduit of the invention (right) are compared in FIG. 9A. Scale bars are 100 μm for both panels and 20 μm forth the insets. Native nerve tissue was comprised of axon bundles separated by connective tissue (white regions). The lateral axon cross section of the native nerve exhibited large, thick dark brown staining due to the presence of myelinated sheaths around the axon extensions (inset). Comparatively, the sizes of the lateral axon cross section of the extending axons within the chitosan-PCL conduits were smaller and stained brown indicating the presence of young unmyelinated processes. Images of silver-stained longitudinal sections of native (left) and new nerves formed in a representative chitosan-PCL (chitosan:PCL=40:60) nanofibrous conduit of the invention (right) are compared in FIG. 9B. The newly formed nerves display axonal elongation at the nerve tip (indicated by the white triangle) and the tip of its growing nerve inside the conduit. Normal distributions of axons are seen in the chitosan-PCL conduit. Histological analyses of the explants demonstrated regeneration of nerve fibers. These results indicate that the nanofibrous conduits of the invention are effective for regenerating nerve in vivo.

The present invention provides nanofibers from a blend of a natural and a synthetic polymer and represents a significant advancement in development of composite materials with desired structural and materials properties. The chitosan-poly (caprolactone) nanofiber of the invention exhibits excellent structural stability, and mechanical and biological properties favorable for biomedical applications. The combination of PCL's structural stability with chitosan's bioactivity in a stable phase miscible form offers a new nanofibrous platform.

The fibers of the invention can be advantageously used in tendon, ligament, bone, cartilage, skin, blood vessel, and muscle tissue engineering.

The following examples are provide for the purpose of illustrating, not limiting the invention.

EXAMPLES

Example 1

The Preparation of Representative Chitosan-PCL Nanofibrous Conduits

In this example, the preparation of representative chitosan-PCL nanofibrous conduits of the invention by electrospinning is described.

5 wt % chitosan (medium molecular weight chitosan from Sigma Chemical Co., viscosity 200-800 cP in 1% acetic acid, deacetylation of 75-85%) solutions were prepared at elevated temperature which weakens intermolecular forces between polymer chains and increases the solution solubility. The chitosan was fully dissolved by refluxing the chitosan/TFA mixture for 3 h at 80° C. 10 wt % PCL (Sigma Chemical, Co., Mn 70-90 kDa) solutions were prepared by dissolving PCL in TFE (Sigma). The two solutions were mixed at varying weight ratios of chitosan:PCL and vortexed for two minutes. Acidic hydrolysis of the PCL by TFA limits the lifespan of the mixture for electrospinnability to about one hour after component mixing, requiring component mixing immediately prior to the electrospinning process, requiring component mixing immediately prior to the electrospinning process, or continued mixing of the two solutions during the electrospinning in production settings. This means that the mixture (not two individual solutions) should be made within one hour before electrospinning.

The electrospinning instrumentation used is described in N. Bhattarai, et al., *Advanced Materials* 18:1463, 2006, and N. Bhattarai, et al., *Biomaterials* 26:6176, 2005, each expressly incorporated herein by reference in its entirety. Briefly, a DC voltage of 17-20 kV with low output current was applied between a syringe tip and a cylindrical collector covered with aluminum foil at a distance of 17-20 cm. The cylinder had a diameter of 7 cm and was driven by a DC motor with controllable speed. The solution for electrospinning was fed into a 3 mL disposable syringe fitted with a pipette tip of 0.5 mm in diameter. The solution feed was driven by gravity and the feed speed was controlled by the tilt angle of the syringe. For all experiments, solution flow rate was maintained at 0.95 mL/h. During the spinning process, the pendant droplet at the syringe tip was split by a repulsion force set by the charge in the droplet, and formed a jet of a cone-like shape traveling towards the collector in the form of a nonwoven mat. The spinning was done at room temperature and the as-spun nanofibers were dried under vacuum at room temperature.

The nanofibrous conduits were fabricated by depositing the fibers on a stainless steel rod collector. The tubular constructs were removed from the rod and dried for 24 hours prior to testing. Alternatively, fibrous mats were collected on larger-diameter spindles.

Example 2

The Preparation of Chitosan-PCL Cast Conduits

In this example, the preparation of chitosan-PCL cast conduits are described.

The solvent cast conduits were prepared by dip coating. A 16 g needle was dipped into the chitosan-PCL mixture, allowed to dry at room temperature (5 min), then heated to 60° C. (15 min). This coating process was repeated several times depending on the thickness of the coating to be made. The samples were heated to 60° C. for 2 hours, cooled to −20° C. for 30 min, and then warmed to room temperature. The tube was then removed from the needle and stored under ambient conditions prior to use.

Example 3

The Preparation of Comparative Nanofibers and Films

In this example, the preparation of other nanofibers and films for comparison to representative chitosan-PCL nanofibers and structures of the invention are described.

PLGA and PCL nanofibers, and chitosan-PCL films were prepared for comparison to chitosan-PCL nanofibers. 7 wt % PLGA and 10% PCL were dissolved in DMF and TFE, respectively. Prior to spinning, the PLGA solution was diluted by 40 wt % DMSO. For chitosan-PCL film, 2 wt % PCL and chitosan solutions were prepared in TFE and TFA, respectively. A 40:60 chitosan-PCL solution was prepared and vortexed for 2 min. A 200 µL solution was deposited on 12 mm round cover slips and spin coated at 500 rpm for 30 seconds. After coating, the spinning was continued at 1000 rpm for one minute to remove excess solution and expedite solvent evaporation. After drying, the film was neutralized with 14% ammonium hydroxide for 15 min and rinsed with copious amounts of DI water to remove residual base.

Example 4

Microscopic Imaging of Nanofibrous Structures

In this example, the microscopic imaging of nanofibrous structures is described.

Electrospun structures were soaked in 14 wt % ammonium hydroxide solution for 5 min and rinsed with DI water three times. The samples were dried under reduced pressure at room temperature. Nanofibrous morphology was examined by SEM (JEOL JSM-840A ???) at an accelerating voltage of 10 kV after sputter-coated with Au/Pd. TEM was used to observe internal features of the nanofibers. A thin nanofibrous membrane was sandwiched in a PELCO® folding grid and examined at the membrane edge.

Figure 3B:
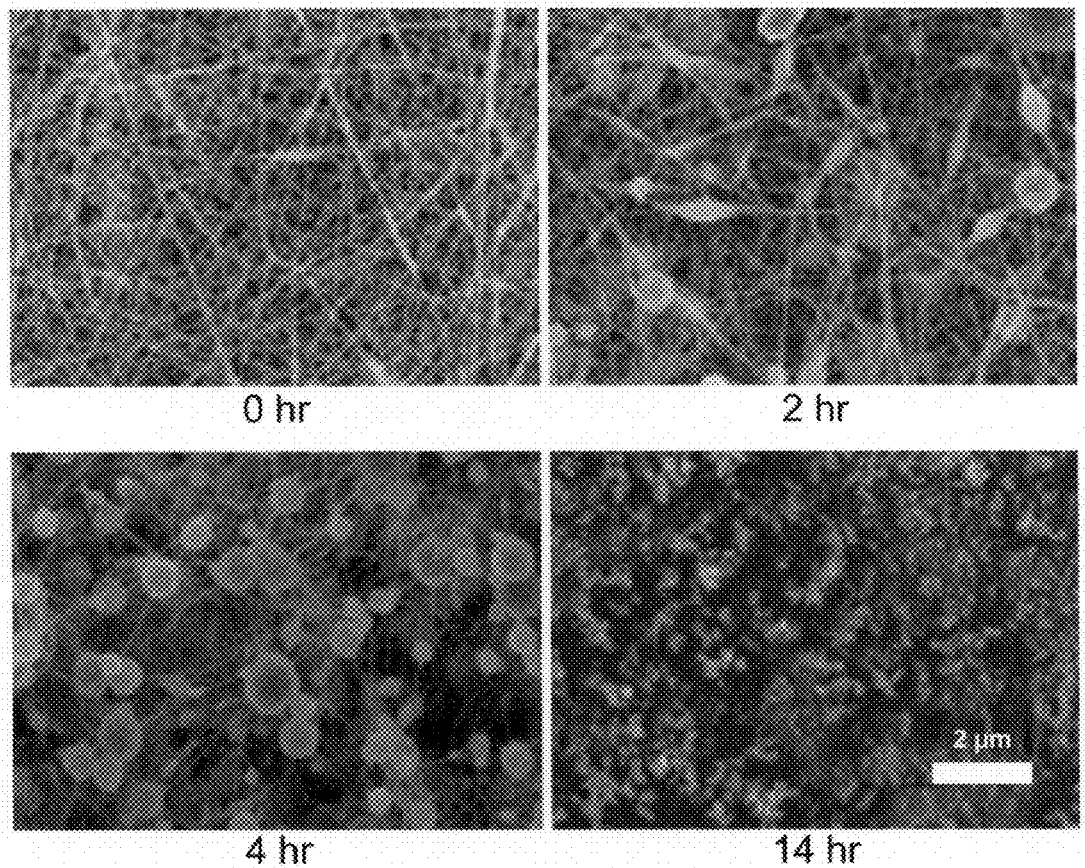
FIG. 3B compares SEM images of chitosan-PCL nanofibers prepared with chitosan-PCL solutions (chitosan:PCL=40:60) at different storage times (0, 2, 4, and 14 hr), showing that the viscosity and storage time of the solution directly influence spinnability, and only solutions with short storage time yielded bead-free structures. Fiber morphology obtained from the solution with a storage time less than 5 min is indicated as 0 hr.
Figure 4A:
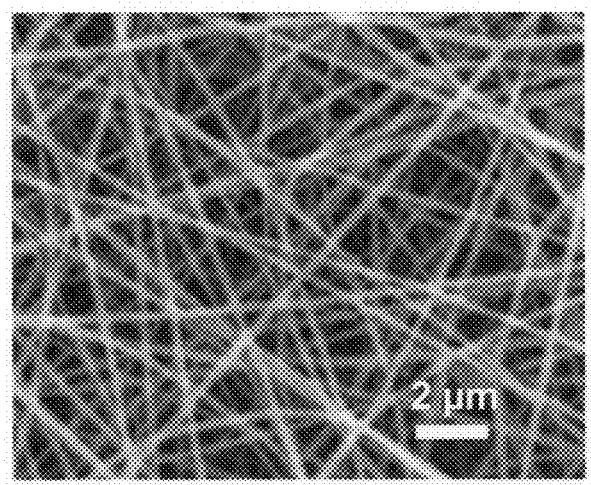
FIG. 4A is an SEM image of representative chitosan-PCL nanofibers of the invention (chitosan:PCL=40:60) showing bead-free fiber morphology.
Figure 4B:
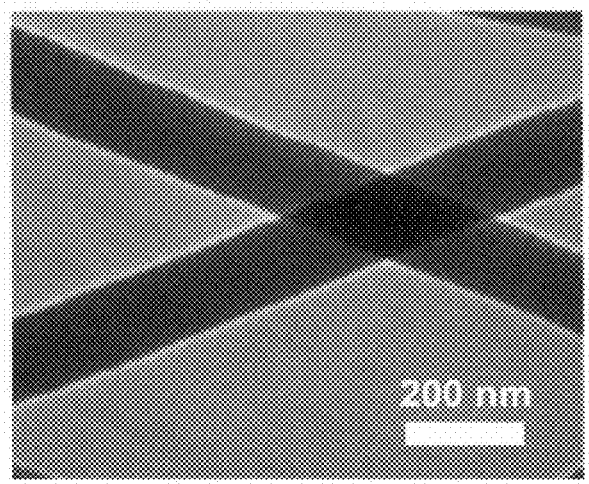
FIG. 4B is a TEM micrograph of representative chitosan-PCL nanofibers of the invention (chitosan:PCL=40:60) showing no visible phase segregation or porosity.
Figure 4C:
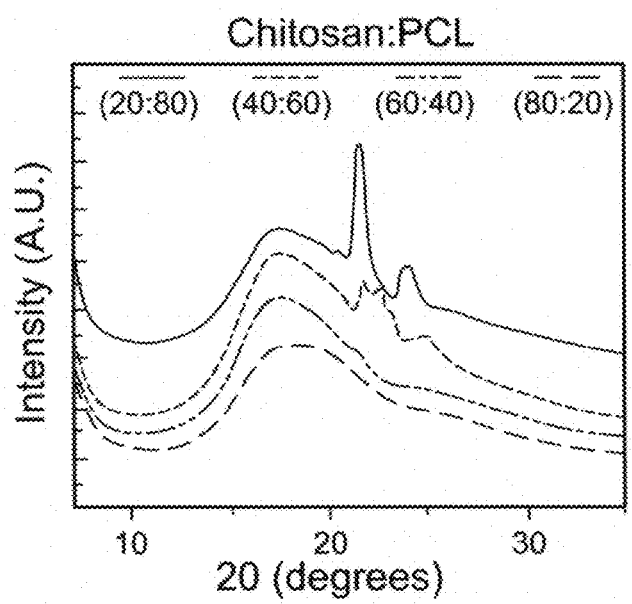
FIG. 4C are WAXS patterns of representative blend nanofibers with varying component ratios of chitosan to PCL (20:80, 40:60, 60:40, and 80:20); the blends with a ratio of 40/60 or greater showed significantly reduced crystallinity signifying increased miscibility FIGS. 4D and 4E compare SEM and TEM images, respectively, of representative chitosan-PCL nanofibers of the invention (chitosan:PCL=40:60) as prepared, and after 7 and 30 days incubation with lysozyme-PBS solution revealing no apparent morphological change, phase segregation, or decomposition of the fiber constructs, demonstrating structural and chemical stability.

FIGS. 2A-2D are SEM images of representative chitosan-PCL nanofibers of the invention prepared with different ratios of chitosan to PCL (chitosan:PCL=40:60, 60:40, 70:30, and 80:20). FIG. 3B compares SEM images of chitosan-PCL nanofibers prepared with chitosan-PCL solutions (chitosan:PCL=40:60) at different storage times (0, 2, 4, and 14 hr). FIG. 4A is an SEM image of representative chitosan-PCL nanofibers of the invention (chitosan:PCL=40:60) showing bead-free fiber morphology. FIG. 4B is a TEM micrograph of representative chitosan-PCL nanofibers of the invention (chitosan:PCL=40:60).

Example 5

Stability Testing of Nanofibrous Structures

In this example, stability testing (degradation) of nanofibrous structures is described.

Dried chitosan-PCL nanofibrous membranes were cut into squares (15×15 mm²), neutralized in 1 N NaOH, washed with deionized water, sterilized in absolute alcohol (10 min incubation), and washed thoroughly with PBS. Membrane integrity was then tested by incubating samples in 15 mL PBS (pH=7.5, 37° C.) with 1 mg/ml lysozyme from chicken egg white (Sigma). The buffer was replaced every 3 days. The samples were taken out from the solution at specified intervals and examined for morphological changes (degradation).

Figure 4D:
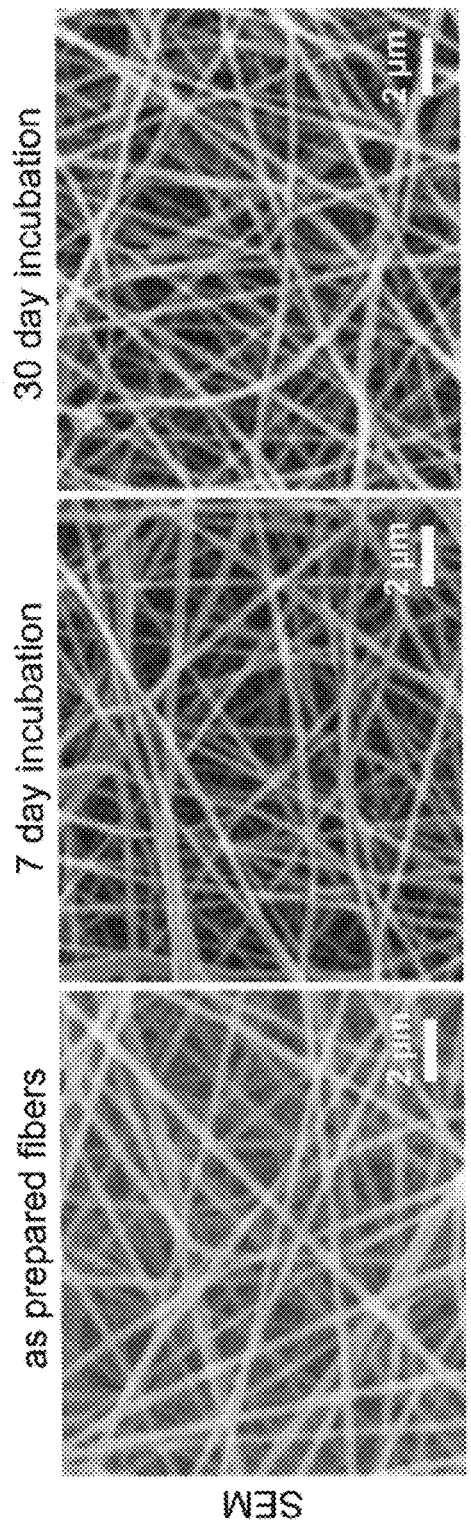
Figure 4E:
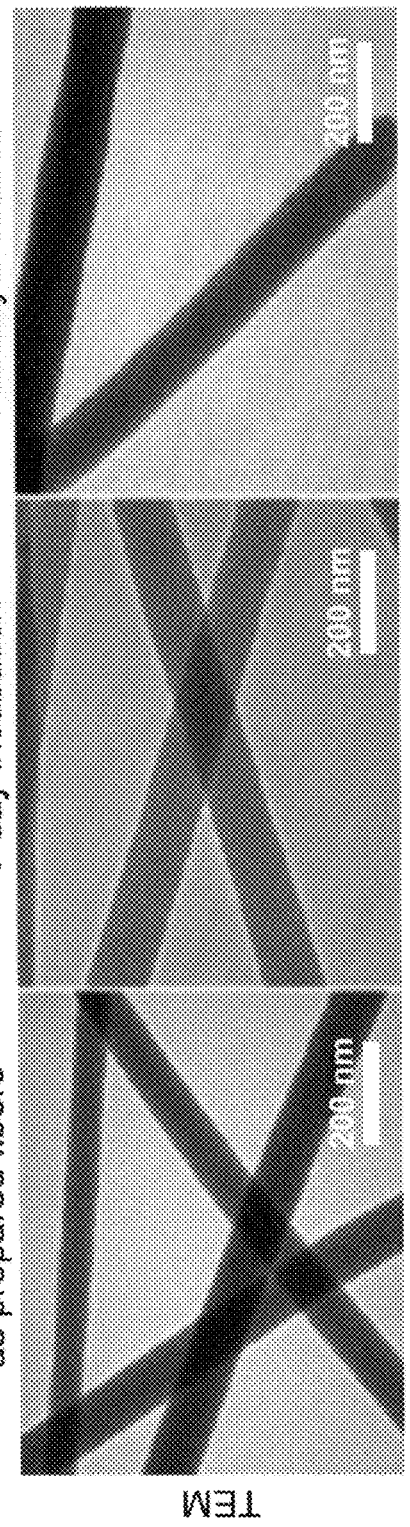

FIGS. 4D and 4E compare SEM and TEM images, respectively, of representative chitosan-PCL nanofibers of the invention (chitosan:PCL=40:60) as prepared, and after 7 and 30 days incubation with lysozyme-PBS solution. No apparent morphological change, phase segregation, or decomposition of the fiber constructs was observed demonstrating their structural and chemical stability.

Example 6

Characterization of Nanofibrous Structures

In this example, X-ray diffraction, infrared spectroscopy, and differential scanning calorimetry methods for characterizing the nanofibrous structures are described.

WAXS patterns were acquired over a diffraction angle of $2\theta=5\text{-}45°$ at room temperature with a wide angle X-ray diffractometer with CuKα radiation, operated at 40 kV and 20 mA. WAXS patterns of representative nanofibers of the invention are compared in FIG. 4C.

Polarized FTIR spectra of 200 scans at 4 cm$^{-1}$ resolution were obtained using a Nicolet 5DX spectrometer. Dried nanofibrous samples were mounted and the system purged with nitrogen before testing. FTIR spectra of nanofibers of the invention are compared in FIG. 5B.

Thermal properties of chitosan-PCL nanofiber constructs were studied by differential scanning calorimetry under a nitrogen atmosphere at a heating rate of 10° C./min. All the samples were quenched under liquid nitrogen before the heating scans. DSC thermograms of nanofibers of the invention are compared in FIG. 5A.

Example 7

Biological Properties of Representative Nanofibrous Structures

In this example, the biological properties of representative nanofibrous structures of the invention are described.

Cell transfection. Schwann cells were transfected with the GFP plasmid (p-EGFP-N1, 94% efficiency) using the effectene transfection reagent kit (Qiagen). Schwann cells were plated on a 10-cm Petri dish (BD Labware; 1.5×10$^6$ cells/dish) in DMEM media 18 hrs before transfection (all DMEM enriched with 10% FBS; Invitrogen). A mixture of DNA condensation buffer (300 μl), plasmid DNA (2 μg), and Enhancer (16 μl) was prepared immediately prior to transfection. Cells were incubated in the mixture for 5 min at room temperature, treated with the effectene reagent (100 μl added to mixture), allowed to stand for 5 min, and then given DMEM media (7000 μl DMEM added to mixture). 24 hours after transfection the cells were given fresh DMEM media. For rapid selection of cells that stably and uniformly expressed GFP, a two-tiered selection process was used. Two days after transfection, GFP+ cells were initially selected by fluorescence activated cell sorting (FACS; Vantage SE) and then isolated after treating the cell population with G418-rich media (1 mg/ml) for 2 weeks. After the selection process flow cytometry identified>90% of all cells expressed GFP activity (BD Canto).

Cell culture, attachment, and proliferation. Fiber samples were wrapped over 12 mm round cover slips and secured with 3.5 wt % poly-L-lactic acid in hexafluoroisopropanol. Prior to cell culture, the samples were sterilized overnight with ethanol and equilibrated with DMEM (10 v/v % FBS, 100 units penicillin-streptomycin antibiotics) for 24 hrs. PC12 cells were obtained from the American Type collection and maintained in RPMI 1640 medium supplemented with 10% FBS. PC 12 cells were trypsinized for 10 min to dissociate cell clusters, and resuspended in F12K media (1% horse serum, 100 units of penicillin-streptomycin, 200 ng/mL NGF). GFP-Schwann cells were resuspended in DMEM (10 v/v % FBS, 100 units penicillin-streptomycin, 1 mg/mL G418 sulfate).

25,000 PC12 cells and 12,500 cells of GFP-Schwann cells were separately seeded on PCL (Example 3), chitosan-PCL (Example 1), and PLGA (Example 3) nanofibers, chitosan-PCL films (Example 2) and glass cover slips in 24 well plates. All samples were prepared in triplicate for each measurement. After 1, 3, and 5 days of culture, the number of Schwann and PC12 cells adhered on the materials were measured with an alamarBlue assay (Biosource). The samples were washed with warm, phenol-free DMEM and incubated with 10 v/v alamarBlue in phenol-free DMEM for 1.5 hrs. 250 μL of culture medium was removed and placed in a 96 well-plate. The absorbance was measured at 570 and 600 nm using a spectrophotometer and the % reduction of the alamar-Blue solution was calculated. Known cell quantities of both cell lines were also tested to correlate % Reduction to cell number.

Figure 6C:
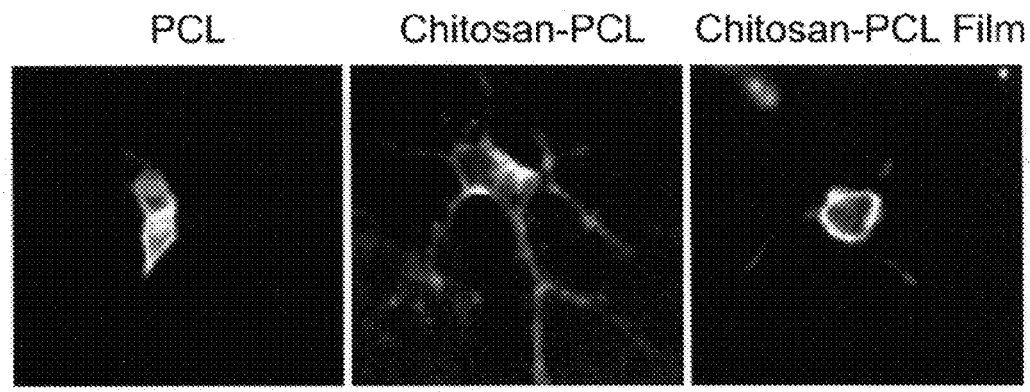
FIG. 6C compares confocal images of PC12 cells on PCL nanofibers (PCL), chitosan-PCL nanofibers (Chitosan-PCL), and a chitosan-PCL film (Chitosan-PCL Film) stained with an NGF receptor (green) antibody and DAPI (blue).

FIG. 6C compares confocal images of PC12 cells on PCL nanofibers (PCL), chitosan-PCL nanofibers (Chitosan-PCL), and a chitosan-PCL film (Chitosan-PCL Film) stained with an NGF receptor (green) antibody and DAPI (blue).

Figure 6D:
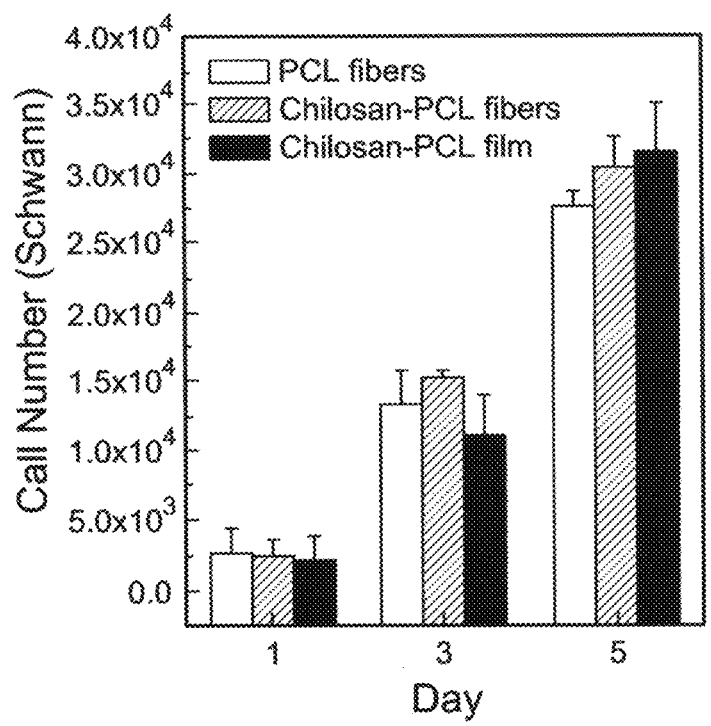
FIG. 6D is a graph comparing the number of Schwann cells on PCL nanofibers (PCL), chitosan-PCL nanofibers (Chitosan-PCL), and a chitosan-PCL film (Chitosan-PCL Film) as a function of culture time, assessed by the alamarBlue assay. Values are means of three independent experiments; error bars correspond to standard error of mean.
Figure 6E:
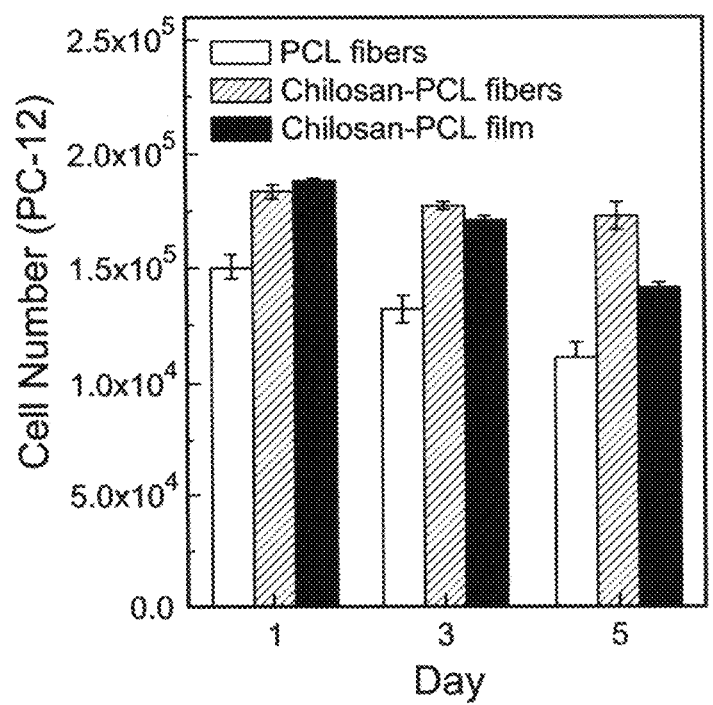
FIG. 6E is a graph comparing the number of PC12 cells on PCL nanofibers (PCL), chitosan-PCL nanofibers (Chitosan-PCL), and a chitosan-PCL film (Chitosan-PCL Film) as a function of culture time, assessed by the alamarBlue assay. Values are means of three independent experiments; error bars correspond to standard error of mean.

FIGS. 6D and 6E are graphs comparing the number of Schwann cells and PC12 cells, respectively, on PCL nanofibers (PCL), chitosan-PCL nanofibers (Chitosan-PCL), and a chitosan-PCL film (Chitosan-PCL Film) as a function of culture time, assessed by the alamarBlue assay.

Nanofibrous conduits were sterilized in 75% ethanol for 24 hrs and rinsed with PBS four times. Schwann cells were seeded on the conduit at 1×10$^6$ cells/mL and cultured for 7 days prior to PC12 co-culture at a concentration of 1×10$^6$ cells/mL (culture media supplemented with 200 ng/mL NGF). After 7 days of co-culturing Schwann and PC12 cells, three samples were harvested for SEM imaging. Four days later, the remaining samples were collected for immunochemistry study.

Figure 7E:
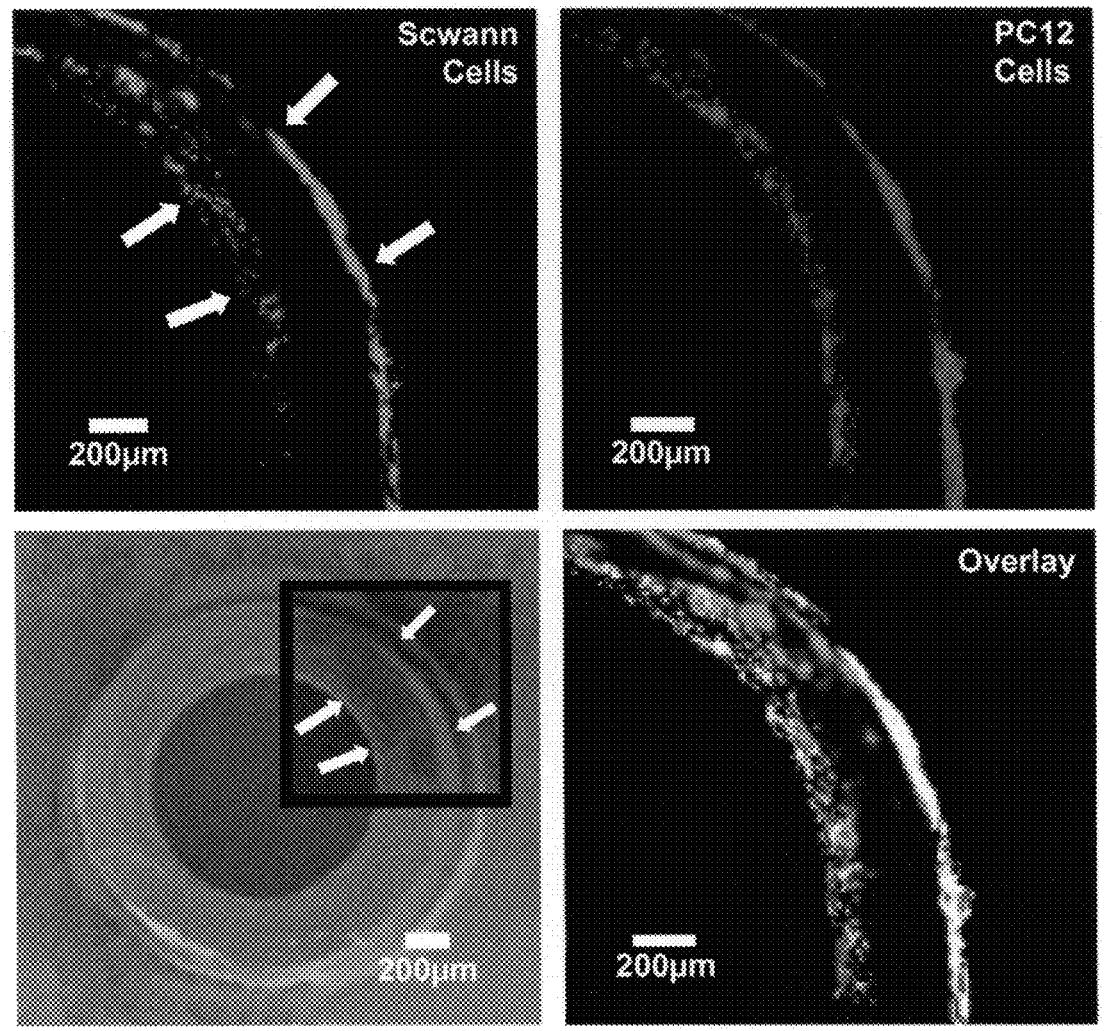
FIG. 7E compares confocal images of Schwann cells (green) and PC12 cells (red) co-cultured on representative chitosan-PCL nanofibrous conduits of the invention showing adherence of GFP-transfected Schwann (indicated by arrows) and PC12 cells on the inner and outer surfaces of the conduit.
Figure 7F:
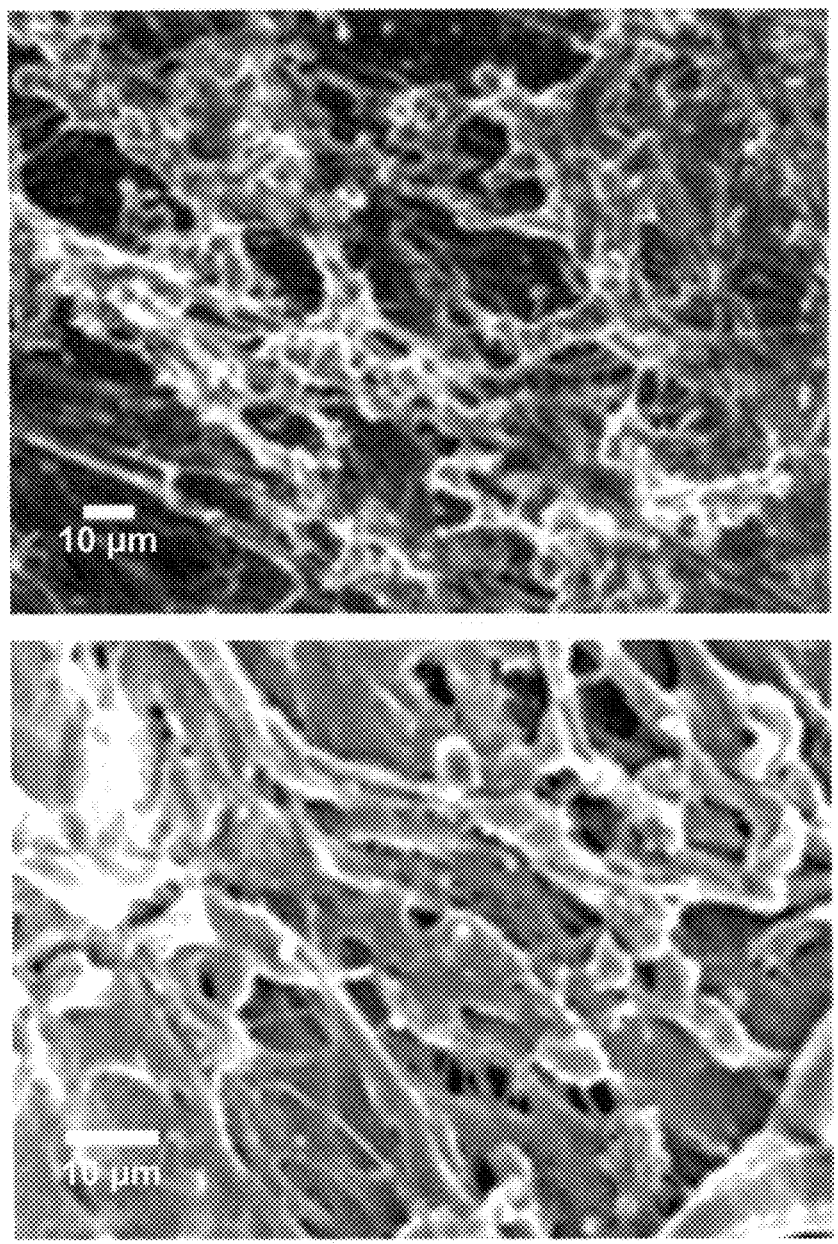
FIG. 7F compares SEM micrographs of Schwann cells and PC12 cells co-cultured on the surface of a representative chitosan-PCL nanofibrous conduit of the invention at lower (top) and higher (bottom) magnifications showing neurite-like outgrowth of PC12 cells.
Figure 8A:
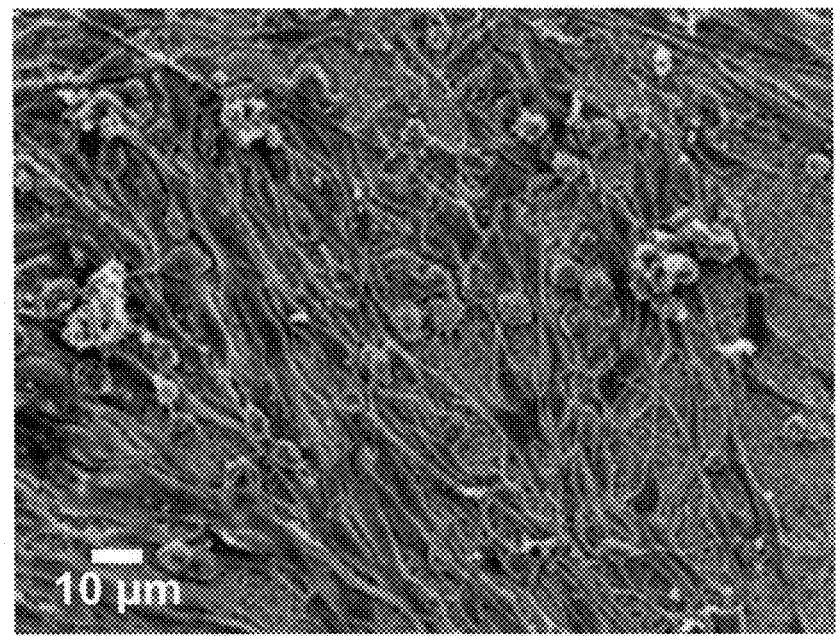
FIGS. 8A and 8B compare SEM micrographs of Schwann cells and PC12 cells co-cultured for 7 days on representative chitosan-PCL nanofibers (chitosan:PCL 40:60) of the invention at lower (8A) and higher (8B).
Figure 8B:
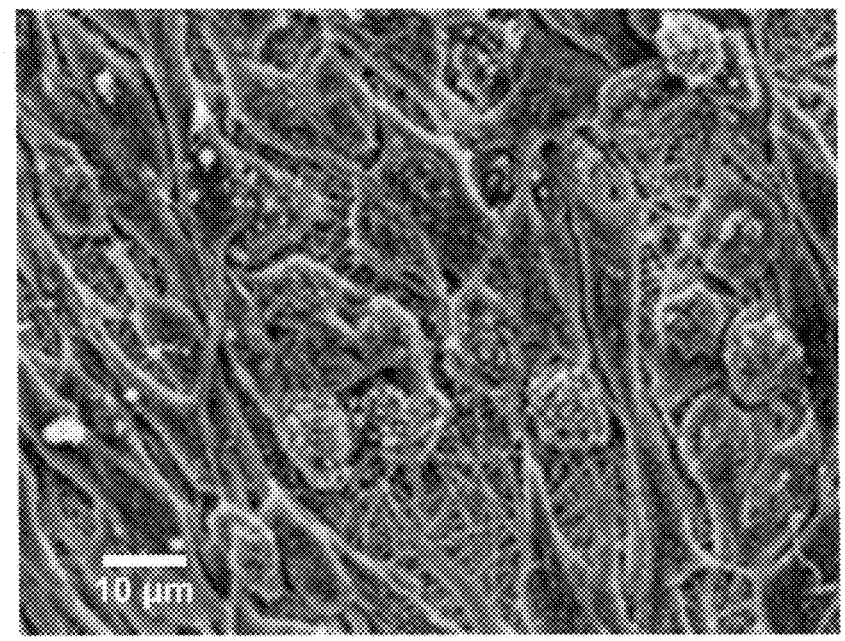

FIG. 7E compares confocal images of Schwann cells (green) and PC12 cells (red) co-cultured on representative chitosan-PCL nanofibrous conduits of the invention showing adherence of GFP-transfected Schwann (indicated by arrows) and PC12 cells on the inner and outer surfaces of the conduit.

Statistical analysis of the PC12 proliferation was performed using one-way analysis of variance (ANOVA). P values less than 0.05 were considered statistically significant, and differences between samples within the groups were evaluated using a Student's t-test analysis ($p<0.05$).

SEM analysis of cell morphology. Scanning electron microscopy was performed to examine Schwann and PC12 cell attachment. Samples were removed from culture media, rinsed with PBS and fixed with Karnovsky's fixative overnight. After fixing, samples were briefly rinsed with DI water and dehydrated with sequential rinses of 50, 75 and 100% ethanol for 15 min each. Samples were sputter-coated with Au/Gd for 30 seconds at 18 mA and imaged with a JSM 7000F.

FIGS. 6A and 6B are SEM images comparing Schwann (6A, 1 day) and PC12 (6B, 7 days) cell adherence and growth on a PCL fibrous structure (PCL) and representative chitosan-PCL structures of the invention (chitosan:PCL=40:60) (Chitosan-PCL and Chitosan-PCL Film). FIG. 7F compares SEM micrographs of Schwann cells and PC12 cells co-cultured on the surface of a representative chitosan-PCL nanofibrous conduit of the invention at lower (top) and higher (bottom) magnifications showing neurite-like outgrowth of PC12 cells.

Immunocytochemistry. Samples cultured with PC12 cells were removed from cell culture medium and fixed in paraformaldehyde overnight at 4° C. The samples were rinsed with ice cold PBS three times for 5 min each and blocked with 3% bovine serum albumin (BSA) in PBS for 30 min. The samples were then incubated with a LANGF receptor antibody (200 μg/ml; Abcam) in PBS for 1 hr at room temperature. Following incubation, the samples were immersed in PBS for 30 min prior to incubation in the presence of FITC-labeled rabbit polyclonal anti-mouse antibody (1:500 dilution in PBS; Abcam) for 1 hr. Finally, the samples were counterstained with a 1:500 solution of DAPI in PBS for 10 min, and rinsed with PBS prior to microscopy with a Zeiss 510 Zeta Microscope (Carl Zeiss).

Example 8

Mechanical Properties of Representative Nanofibrous Structures

In this example, the mechanical properties of representative nanofibrous structures of the invention are described.

Mechanical testing. Both wet and dry nanofibrous conduits were evaluated for stress-strain response using a micro-tensile testing machine designed for small samples. For tensile strength tests, conduits were cut and opened to form a rectangular sheet. Wet samples were prepared by incubating the samples in PBS for 24 hrs at 37° C. The tensile modulus was calculated from the stress verses strain curve.

Young's modulus and breaking strength for representative conduits of the invention are compared to PLGA and collagen conduits in FIGS. 7A and 7B.

Compression study was conducted using a load-strain profile on a Dynamic Mechanical Analyzer. Tubular samples (~15 mm length, 1.5 mm inner diameter and 0.2 mm wall thickness) were set lengthwise in the testing apparatus. Compressive strength was measured as a force applied perpendicular to the axis of the sample and loads were recorded at strains of 10 to 50%. A preload force of 60 mN was applied to each sample with a force ramp rate of 500 mN/min and an upper force limit of 6110 mN. Three samples for each condition were tested at 25° C. and are presented with error values representing standard error of measurement (SEM) for each sample.

10% and 50% compression for representative conduits of the invention are compared to PLGA and collagen conduits in FIGS. 7C and 7D.

Differences in mechanical strength were determined by Student's t-test analysis ($p<0.05$).

Example 9

In Vivo Nerve Regeneration with Representative Nanofibrous Conduits

In this example, in vivo nerve regeneration (rat sciatic defect model) with representative conduits of the invention is described.

Sprague Dawley (SD) rats (8) were split into two groups (with and without chitosan-PCL conduits prepared as described in Example 1). Gas anesthesia (isoflurane) was employed to induce and maintain anesthesia during surgery. After anesthesia was administered in an induction chamber, the rat was relocated using an adapter mask for continued anesthesia. The front toes were stimulated to test the effect of anesthesia. Fur was removed and skin disinfected with iodine tincture and alcohol on the right thigh prior to incision. A 3-4 cm incision was made over the dorsum of the right thigh. Incisions along the intramuscular planes exposed the right sciatic nerve and a 15 mm segment of the nerve was removed. The proximal and distal endings of the nerve were secured with 8/0 monofilament nylon suture to a depth of about 1 mm from the edge of the conduit. The skin was closed with a 4/0 silk suture after the neurography. Analgesia was administered soon after surgery. All rats were closely observed for one week after surgery and sutures were removed one week later. One month after the implantation, the rats were euthanized by carbon dioxide followed by cervical dislocation. The implants were exposed and the implanted nerve conduits removed with proximal and distal native nerve tissue. The explanted conduits were resectioned, fixed with 4% paraformaldehyde, and sliced with a microtome (5 µm thickness). The thin sections were then stained with silver. All histological staining was prepared following the standard procedure, and observed by optical microscopy.

Figure 9A:
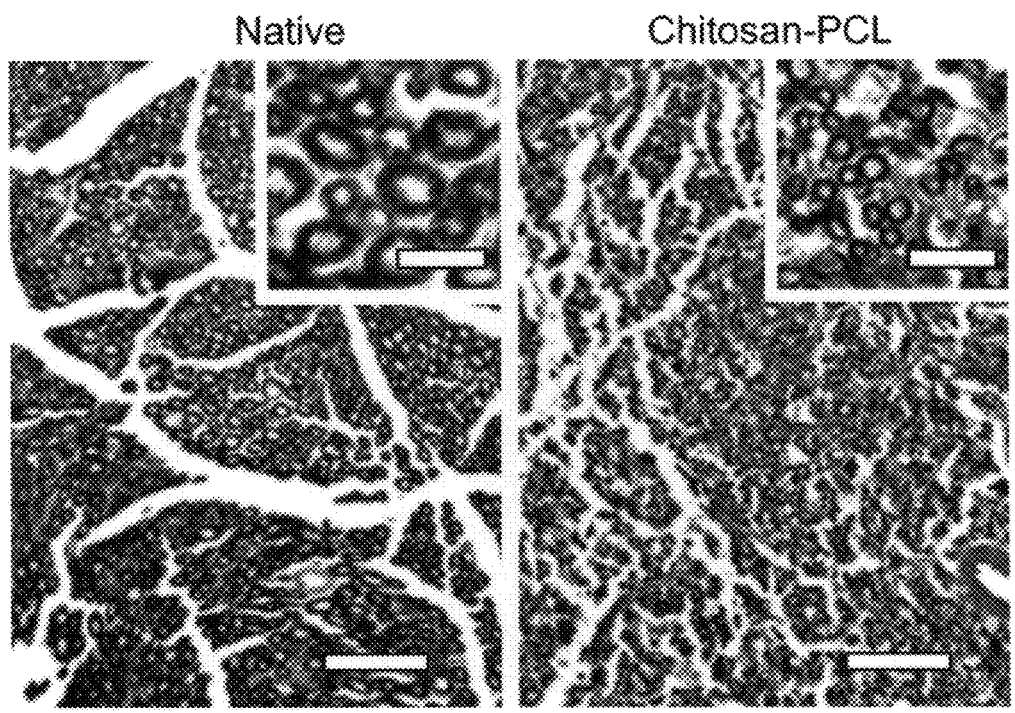
FIG. 9A compare images of silver-stained cross sections of native (left) and new nerves formed in a representative chitosan-PCL (chitosan:PCL=40:60) nanofibrous conduit of the invention (right).
Figure 9B:
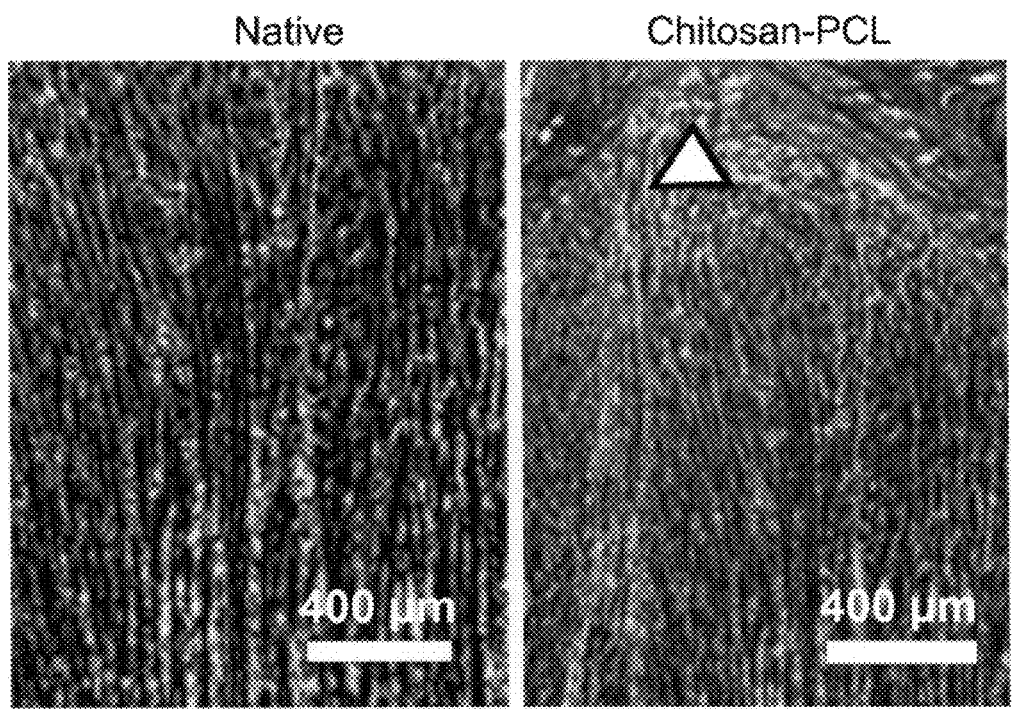
FIG. 9B compare images of silver-stained longitudinal sections of native (left) and new nerves formed in a representative chitosan-PCL (chitosan:PCL=40:60) nanofibrous conduit of the invention (right).

Images of silver-stained cross and longitudinal sections of native (left) and new nerves formed in a representative chitosan-PCL (chitosan:PCL=40:60) nanofibrous conduit of the invention (right) are compared in FIGS. 9A and 9B, respectively.

While illustrative embodiments have been illustrated and described, it will be appreciated that various changes can be made therein without departing from the spirit and scope of the invention.

The embodiments of the invention in which an exclusive property or privilege is claimed are defined as follows:

1. A hollow fibrous conduit for promoting regeneration of a severed nerve, comprising a first end capable of coapting the conduit to a first end of a severed nerve and a second end capable of coapting the conduit to a second end of the severed nerve, the hollow fibrous conduit comprising chitosan-poly(caprolactone) nanofibers, wherein the chitosan-poly(caprolactone) nanofibers comprise about 20 to about 80 percent by weight chitosan and about 80 to about 20 percent by weight poly(caprolactone), and wherein the chitosan-poly(caprolactone) nanofibers are a miscible polymer blend prepared from a chitosan-poly(caprolactone) solution that is suitable for electrospinning.

2. The conduit of claim 1, wherein the chitosan-poly(caprolactone) nanofibers have a diameter of from about 50 to about 2000 nm.

3. The conduit of claim 1 having a length from about 0.1 to about 100 cm.

4. The conduit of claim 1 having an inner diameter from about 1 to about 10 mm.

5. The conduit of claim 1 having a thickness from about 0.1 to about 1.0 mm.

6. The conduit of claim 1 having a modulus from about 0.05 to about 1000 MPa in the dry state.

7. The conduit of claim 1 having a modulus from about 0.5 to about 200 MPa in the wet state.

8. The conduit of claim 1 having a breaking strength from about 0.5 to about 100 MPa in the dry state.

9. The conduit of claim 1 having a breaking strength from about 0.1 to about 50 MPa in the wet state.

10. The conduit of claim 1 having a compressive strength from about 0.1 to about 20 N at 10% compression in the wet state.

11. The conduit of claim 1 further comprising a neurotrophic agent.

12. The conduit of claim 1 further comprising FK506, aFGF, PFGF, 4-methylcatechol, NGF, BDNF, CNTF, MNGF, NT-3, GDNF, NT-4/5, CM101, inosine, spermine, spermidine, HSP-27, IGF-I, IGF-II, PDGF, ARIA, LIF, VIP, GGF, IL-1, and MS-430.

13. A chitosan-poly(caprolactone) nanofiber comprising from about 20 to about 80 percent by weight chitosan and from about 80 to about 20 percent by weight poly(caprolactone), wherein the chitosan-poly(caprolactone) nanofiber is a miscible polymer blend prepared from a chitosan-poly(caprolactone) solution that is suitable for electrospinning.

14. The chitosan-poly(caprolactone) nanofiber of claim 13, wherein the nanofiber has a diameter of from about 50 to about 2000 nm.

15. The chitosan-poly(caprolactone) nanofiber of claim 14, wherein the nanofiber has a diameter of from about 150 to about 600 nm.

16. The chitosan-poly(caprolactone) nanofiber of claim 13, wherein the chitosan has an average molecular weight of from about 50 to about 1000 kDa.

17. The chitosan-poly(caprolactone) nanofiber of claim 13, wherein the chitosan has a degree of deacetylation of from about 75 to about 85 percent.

18. The chitosan-poly(caprolactone) nanofiber of claim 13, wherein the poly(caprolactone) has an average molecular weight of from about 20 to about 100 kDa.

19. The chitosan-poly(caprolactone) nanofiber of claim 18, wherein the poly(caprolactone) has an average molecular weight of from about 70 to about 90 kDa.

\* \* \* \* \*